(12) United States Patent
Stepanova et al.

(10) Patent No.: US 12,319,919 B2
(45) Date of Patent: Jun. 3, 2025

(54) SYNTHETIC ETHYLENE-RESPONSIVE BINDING ELEMENT AND USES THEREOF

(71) Applicants: NORTH CAROLINA STATE UNIVERSITY, Raleigh, NC (US); INSTITUTE OF CYTOLOGY AND GENETICS, SIBERIAN BRANCH OF RUSSIAN ACADEMY OF SCIENCES, Novosibirsk (RU)

(72) Inventors: Anna N. Stepanova, Cary, NC (US); Jose M. Alonso, Cary, NC (US); Josefina Patricia Fernandez-Moreno, Raleigh, NC (US); Elena Zemlyanskaya, Novosibirsk (RU); Victor Levitsky, Novosibirsk (RU)

(73) Assignees: NORTH CAROLINA STATE UNIVERSITY, Raleigh, NC (US); INSTITUTE OF CYTOLOGY AND GENETICS, SIBERIAN BRANCH OF RUSSIAN ACADEMY OF SCIENCES, Novosibirsk (RU)

( * ) Notice: Subject to any disclaimer, the term of this patent is extended or adjusted under 35 U.S.C. 154(b) by 184 days.

(21) Appl. No.: 18/002,134

(22) PCT Filed: Jun. 30, 2021

(86) PCT No.: PCT/US2021/039766
§ 371 (c)(1),
(2) Date: Dec. 16, 2022

(87) PCT Pub. No.: WO2022/006203
PCT Pub. Date: Jan. 6, 2022

(65) Prior Publication Data
US 2023/0235346 A1 Jul. 27, 2023

Related U.S. Application Data

(60) Provisional application No. 62/705,516, filed on Jul. 1, 2020.

(51) Int. Cl.
C12N 15/82 (2006.01)
A01H 6/20 (2018.01)
A01H 6/82 (2018.01)

(52) U.S. Cl.
CPC .......... *C12N 15/8238* (2013.01); *A01H 6/20* (2018.05); *A01H 6/823* (2018.05); *A01H 6/825* (2018.05);
(Continued)

(58) Field of Classification Search
None
See application file for complete search history.

(56) References Cited

U.S. PATENT DOCUMENTS 6,232,107 B1 5/2001 Bryan et al.
7,994,406 B2 8/2011 Patell

OTHER PUBLICATIONS

Song, Jinghui, et al. "Biochemical and structural insights into the mechanism of DNA recognition by *Arabidopsis* Ethylene Insensitive3." PLoS One 10.9 (2015): e0137439. (Year: 2015).*

(Continued)

*Primary Examiner* — Weihua Fan
(74) *Attorney, Agent, or Firm* — Myers Bigel, P.A.

(57) ABSTRACT

Provided is a recombinant nucleic acid construct comprising a sequence of Formula I (SEQ ID NO:48): X—$N_1$—$N_2$—$N_3$—$N_4$—$N_5$—$N_6$—$N_7$—$N_8$—$N_9$—$N_{10}$—$N_{11}$—Y as an ethylene binding sequence (EBS). Tandems of two or more directly adjoining EBS are also described, and may be included in an expression cassette useful for modulating the expression of a nucleic acid of interest in a plant in response to plant hormone ethylene.

20 Claims, 10 Drawing Sheets

Specification includes a Sequence Listing.

(52) U.S. Cl.
CPC ...... *C12N 15/8242* (2013.01); *C12N 2320/50* (2013.01)

(56) References Cited

OTHER PUBLICATIONS

Agris Binding Sites List. Retrieved from https://agris-knowledgebase.org/AtcisDB/bindingsites.html on Dec. 15, 2022.
International Search Report and Written Opinion corresponding to PCT/US2021/039766; mailed Aug. 30, 2021 (7 pages).
Brumos, Javier, et al., "An Improved Recombineering Toolset for Plants", The Plant Cell. 32: 100-122 (2020).
Cao, Hui, et al., "Generation of broad-spectrum disease resistance by overexpression of an essential regulatory gene in systemic acquired resistance", Proc. Natl. Acad. Sci. USA. Plant Biology, 95: 6531-6536 (1998).
Chang, Katherine Noelani, et al., "Temporal transcriptional response to ethylene gas drives growth hormone cross-regulation in *Arabidopsis*", eLife. 2: e00675. DOI: 10.7554/eLife.00675 (2013).
Clough, Steven J., et al., "Floral dip: a simplified method for Agrobacterium-mediated transformation of *Arabidopsis thaliana*", The Plant Journal. 16(6): 735-743 (1998).
Faden, Frederik, et al., "Modulating Protein Stability to Switch Toxic Protein Function On and Off in Living Cells", Plant Physiology. 179: 929-942 (2019).
Hao, Dongyun, et al., "Unique Mode of GCC Box Recognition by the DNA-binding Domain of Ethylene-responsive Element-binding Factor (ERF Domain) in Plant", The Journal of Biological Chemistry. 273(41): 26857-26861 (1998).
He, Yubing, et al., "A reporter for noninvasively monitoring gene expression and plant transformation", Horticulture Research. 7:152 (2020).
Heinz, Sven, et al., "Simple Combinations of Lineage-Determining Transcription Factors Prime cis-Regulatory Elements Required for Macrophage and B Cell Identities", Molecular Cell. 38: 576-589 (2010).
Kosugi, Shunichi, et al., "Cloning and DNA-binding properties of a tobacco Ethylene-Insensitive3 (EIN3) homolog", Nucleic Acids Research. 28(4): 960-967 (2000).
Kumar, Deepak, et al., "Development of a salicylic acid inducible minimal sub-genomic transcript promoter from Figwort mosaic virus with enhanced root- and leaf-activity using TGACG motif rearrangement", Gene. 503(1): 36-47 (2012) (Abstract only).
Kurihara, Daisuke, et al., "ClearSee: a rapid optical clearing reagent for whole-plant fluorescence imaging", Development. 142: 4168-4179 (2015).
Levitsky, Victor, et al., "A single ChIP-seq dataset is sufficient for comprehensive analysis of motifs co-occurrence with MCOT package", Nucleic Acids Research. 47(21): e139 (2019).
Mangel, Nathalie, et al., "Enhancement of vitamin B6 levels in rice expressing *Arabidopsis* vitamin B6 biosynthesis de novo genes", The Plant Journal. 99: 1047-1065 (2019).
O'Malley, Ronan C., et al., "Cistrome and Epicistrome Features Shape the Regulatory DNA Landscape", Cell. 165: 1280-1292 (2016).
Patel, Takshay K., et al., "Tomato Plants Overexpressing a Celery Mannitol Dehydrogenase (MTD) Have Decreased Susceptibility to Botrytis cinerea", American Journal of Plant Sciences. 6: 1116-1125 (2015).
Reddy, Chinreddy Subramanyam, et al., "Improving flavour and quality of tomatoes by expression of synthetic gene encoding sweet protein monellin", Mol Biotechnol. 57(5):448-453 (2015) (Abstract only).
Sarrion-Perdigones, Alejandro, et al., "Design and Construction of Multigenic Constructs for Plant Biotechnology Using the GoldenBraid Cloning Strategy", Methods in Molecular Biology. Vol. 1116, Ch. 10, pp. 133-151 (2014).
Sarrion-Perdigones, Alejandro, et al., "GoldenBraid 2.0: A Comprehensive DNA Assembly Framework for Plant Synthetic Biology", Plant Physiology. 162: 1618-1631 (2013).
Sarrion-Perdigones, Alejandro, et al., "GoldenBraid: an iterative cloning system for standardized assembly of reusable genetic modules", PLoS One. 6(7):e21622 (2011).
Solano, Roberto, et al., "Nuclear events in ethylene signaling: a transcriptional cascade mediated by Ethylene- Insensitive3 and Ethylene-Response-Factor1", Genes & Development. 12: 3703-3714 (1998).
Song, Jinghui, et al., "Biochemical and Structural Insights into the Mechanism of DNA Recognition by Arabidopsis Ethylene Insensitive3", PLos One. 10(9): e0137439. doi:10.1371/journal.pone.0137439 (2015).
Stepanova, Anna N., et al., "A Link between Ethylene and Auxin Uncovered by the Characterization of Two Root-Specific Ethylene-Insensitive Mutants in *Arabidopsis*", The Plant Cell. 17: 2230-2242 (2005).
Stepanova, Anna N., et al., "Multilevel Interactions between Ethylene and Auxin in *Arabidopsis* Roots", The Plant Cell. 19: 2169-2185 (2007).
Stepanova, Anna N., "Nuclear events in ethylene signaling in *Arabidopsis thaliana*", A Dissertation in Biology. Retrieved from https://repository.upenn.edu/dissertations/AAI3015380/ on Dec. 15, 2022 (Abstract, Table of Contents and pp. 1-10 only).
Tieman, Denise, et al., "Tomato aromatic amino acid decarboxylases participate in synthesis of the flavor volatiles 2-phenylethanol and 2-phenylacetaldehyde", PNAS. 103(21): 8287-8292 (2006).
Vazquez-Vilar, Marta, et al., "GB3.0: a platform for plant bio-design that connects functional DNA elements with associated biological data", Nucleic Acids Research. 45(4): 2196-2209 (2017).
Vazquez-Vilar, M., et al., "Software-Assisted Stacking of Gene Modules Using GoldenBraid 2.0 DNA-Assembly Framework", Plant Functional Genomics. Methods in Molecular Biology, vol. 1284, Ch. 20, pp. 399-417 (2015).

* cited by examiner

SYNTHETIC ETHYLENE-RESPONSIVE BINDING ELEMENT AND USES THEREOF

CROSS-REFERENCE TO RELATED APPLICATIONS

This application is a 35 U.S.C. § 371 national phase application of International Application Serial No. PCT/US2021/039766, filed Jun. 30, 2021, which claims the benefit of U.S. Provisional Patent Application No. 62/705,516, filed Jul. 1, 2020, the contents of which is incorporated by reference herein in its entirety.

STATEMENT OF GOVERNMENT SUPPORT

This invention was made with government support under grant numbers 1650139 and 1750006 awarded by the National Science Foundation. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5051-983 ST25.txt, 23,504 bytes in size, generated on Sep. 8, 2021, is filed herewith. This Sequence Listing is hereby incorporated herein by reference into the specification for its disclosures.

BACKGROUND

ETHYLENE INSENSITIVE3 (EIN3) transcription factor (TF) is the master regulator of gene expression in response to the plant hormone ethylene that guides plant growth under stress conditions. EIN3 is a transcriptional activator that binds a short nucleotide sequence referred to as EBS (EIN3 binding site) in gene promoters to induce transcription (Solano et al. 1998, Nuclear events in ethylene signaling: a transcriptional cascade mediated by ETHYLENE-INSENSITIVE3 and ETHYLENE-RESPONSE-FACTOR1. *Genes Dev.* 12, 3703-3714; Stepanova, 2007, Multilevel interactions between ethylene and auxin in *Arabidopsis* roots. *Plant Cell* 19, 2169-2185; Kosugi and Ohashi, 2000, Cloning and DNA-binding properties of a tobacco Ethylene-Insensitive3 (EIN3) homolog. *Nucleic Acids Res.* 28, 960-967).

EIN3 tends to bind DNA as a homodimer (Solano et al., 1998), and it has been shown recently that ethylene binding sequence (EBS) inverted repeats with a spacer of 10 bp provide EIN3 binding in vitro with a higher affinity than a single EBS (Song et al., 2015). However, the role of EBS architecture in EIN3 functioning has not been investigated on the whole-genome level.

SUMMARY

Provided herein according to embodiments is a recombinant nucleic acid construct comprising two or more directly adjoining ethylene binding sequences (EBS), wherein each of the EBS is a sequence of Formula I (SEQ ID NO:48):

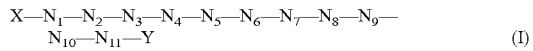

$$X-N_1-N_2-N_3-N_4-N_5-N_6-N_7-N_8-N_9-N_{10}-N_{11}-Y \quad (I)$$

wherein:
$N_1$ is A or G;
$N_2$ is T;
$N_3$ is G, T or A;
$N_4$ is C;
$N_5$ is A;
$N_6$ is A or T;
$N_7$ is T;
$N_8$ is G;
$N_9$ is A, T or C;
$N_{10}$ is A;
$N_{11}$ is T or C; and
X and Y are each independently present or absent and when present is each independently a spacer sequence. In some embodiments, the spacer sequence may be any combination of 2, 5, or 10, to 20, 30 or 50 nucleotides. In some embodiments, the spacer sequence may be 2 to 10 nucleotides, or 4 to 8 nucleotides (e.g., 5 nucleotides).

In some embodiments, the two or more EBS of Formula I comprise two or more of SEQ ID NOS:1-11.

In some embodiments, the two or more EBS of Formula I are operably linked to a core promoter, optionally wherein the core promoter is within 0 to 2,000 base pairs downstream (3') of the two or more EBS of Formula I.

In some embodiments, the two or more EBS of Formula I comprise EBS which are not identical with one another.

In some embodiments, the two or more EBS of Formula I comprise four, five, six, seven eight, nine, ten, eleven or twelve or more EBS of Formula I, and optionally up to 50, 75 or 100 EBS of Formula I.

In some embodiments, the two or more EBS of Formula I does not comprise another transcription factor binding element.

In some embodiments, the construct comprises a sequence selected from the group consisting of SEQ ID NOS:14 and 27-46; and sequences with 90, 91, 92, 93, 94, 95, 96, 97, 98, or 99% identity thereto.

Also provided is an expression cassette comprising the recombinant nucleic acid construct operably linked to a nucleic acid of interest. Further provided is an expression cassette comprising the recombinant nucleic acid construct operably linked to a core promotor, and optionally one or more of a subcellular localization signal (e.g., nuclear localization signal or peroxisome localization signal), a nucleic acid of interest (e.g., a coding sequence of a gene of interest), and a transcriptional terminator.

In some embodiments, the nucleic acid of interest is present and encodes a reporter protein. In some embodiments, the nucleic acid of interest is present and encodes an antioxidant protein, a toxin, a vitamin-biosynthesis protein, a pigment protein, a pathogen defense protein, or a flavor inducing enzyme.

In some embodiments, the expression cassette comprises, from 5' to 3', the recombinant nucleic acid construct as taught herein, the core promotor, the nucleic acid of interest, and the transcriptional terminator.

Further provided is a plant cell comprising the recombinant nucleic acid construct or the expression cassette, and a plant comprising such a plant cell.

A method of modulating the expression of a nucleic acid of interest in a plant in response to ethylene is provided, the method comprising introducing into a plant cell an expression cassette as taught herein to produce a transformed plant cell; regenerating a transformed plant from the transformed plant cell; and exposing the transformed plant, or a plant part or plant cell therefrom, to the ethylene (e.g., by applying ethylene or an ethylene precursor such as 1-aminocyclopropane-1-carboxylic acid (ACC)), whereby the nucleic acid of interest is expressed.

In some embodiments, the recombinant nucleic acid construct and the nucleic acid of interest are integrated into the genome of the plant. In some embodiments, the recombinant nucleic acid construct and the nucleic acid of interest are not integrated into the genome of the plant.

DETAILED DESCRIPTION

Figure 1:
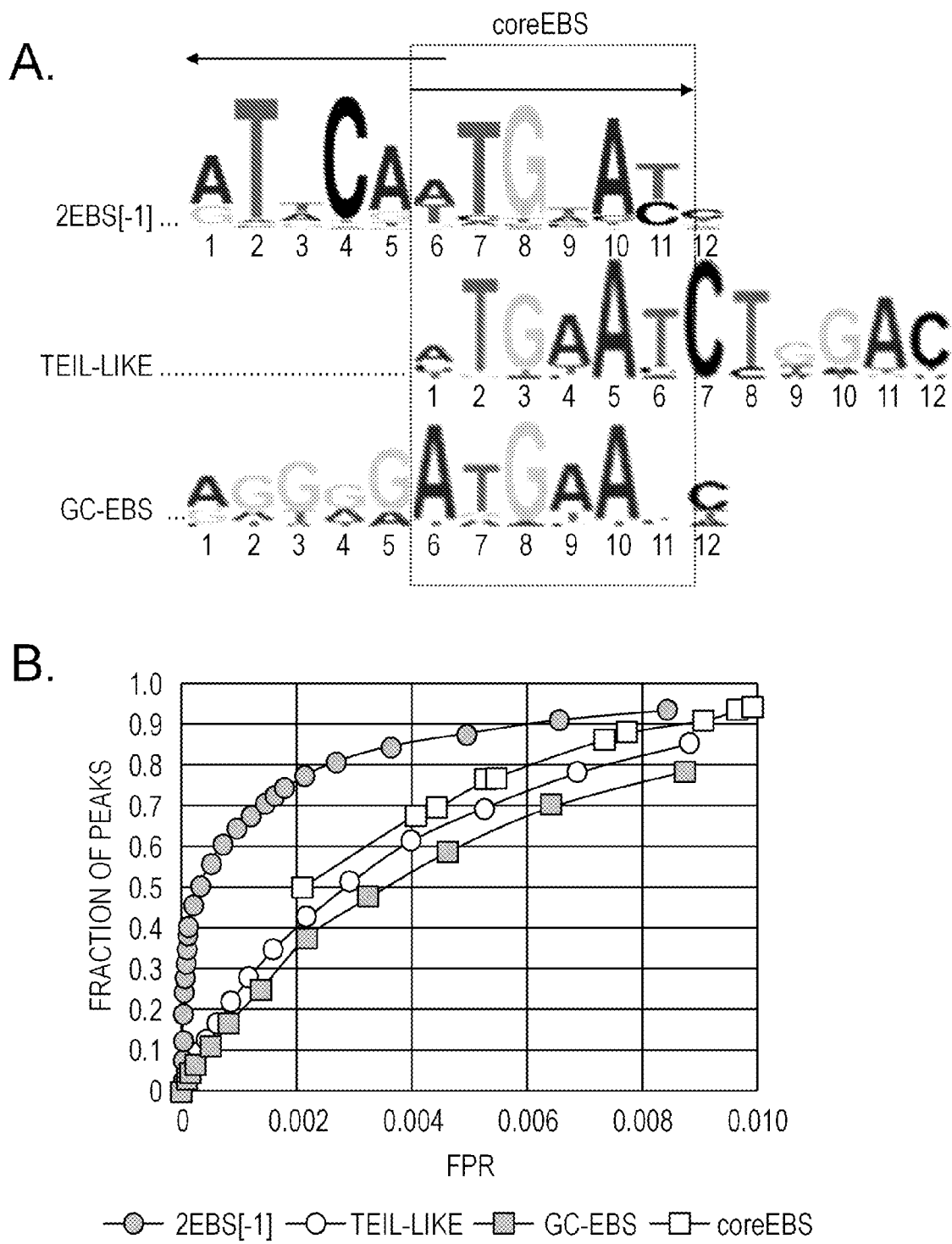
FIG. 1. Enrichment of different EBS configurations in ChIP-seq data. Panel A: EBS-like motifs enriched in EIN3 ChIP-seq peaks. The motifs designated 2EBS(-1) (SEQ ID NO:49), TEIL-like (SEQ ID NO:50) and GC-EBS (SEQ ID NO:51) (see Example 1) were enriched in EIN3 ChIP-seq peaks retrieved from the publicly available SRX215438 dataset (Chang et al., 2013) in this study using the Homer tool (Heinz et al., 2010). Dotted rectangles confine 6 bp-long coreEBS sequences shared between the different motifs. Arrows designate coreEBS sequences within an inverted repeat. Panel B: The occurrence of distinct EBS configurations in ChIP-seq peaks. FPR, false positive rate estimated as the frequency of hits in the whole-genome set of gene promoters.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

A "heterologous" or a "recombinant" nucleic acid is a nucleic acid not naturally associated with a host cell into which it is introduced, including but not limited to nucleic acid sequences that have been altered by changes in one or more base pairs, operative association with another nucleic acid from another species or that is not naturally found associated therewith (such as a coding sequence for a reporter gene), and/or non-naturally occurring multiple copies of a naturally-occurring nucleic acid.

A "native" or "wild type" nucleic acid, nucleotide sequence, polypeptide or amino acid sequence refers to a naturally-occurring or endogenous nucleic acid, nucleotide sequence, polypeptide or amino acid sequence.

A "synthetic" nucleic acid or nucleotide sequence, as used herein, refers to a nucleic acid or nucleotide sequence that is not found in nature but is constructed by human intervention and as a consequence is not a product of nature.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the terms "nucleic acid," "nucleic acid molecule," "nucleic acid construct," "nucleotide sequence"

and "polynucleotide" refer to DNA, RNA, inclusive of RNA/DNA hybrids, the use of less common bases, such as inosine, 5-methylcytosine, 6-methyladenine, hypoxanthine, etc. Other modifications, such as modification to the phosphodiester backbone, or the 2'-hydroxy in the ribose sugar group of the RNA, can also be made. Although the nucleic acid constructs of the present disclosure can be DNA or RNA, they are preferably DNA.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, through human intervention, they exist apart from their native environment and therefore are not products of nature, however, in some embodiments, they can be introduced into and exist in a recombinant host cell.

Except as otherwise indicated, nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end. Thus, for example, an element in the 3' region of a polynucleotide can be located anywhere from the first nucleotide located at the 3' end of the polynucleotide to the nucleotide located halfway through the polynucleotide. An element that is described as being "at the 5'end" or "at the 3'end" of a polynucleotide (5' to 3') refers to an element located immediately adjacent to (upstream of) the first nucleotide at the 5' end of the polynucleotide, or immediately adjacent to (downstream of) the last nucleotide located at the 3' end of the polynucleotide, respectively.

Any polynucleotide and/or nucleic acid construct useful with this invention may be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species-specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function (and in some embodiments, the same structure) as that encoded by the original nucleotide sequence. Thus, in some embodiments of the invention, polynucleotides and/or nucleic acid constructs useful with the invention may be codon optimized for expression in the particular organism/species of interest.

A "promoter" is a nucleotide sequence that controls or regulates the transcription of another nucleotide sequence (i.e., a coding sequence) that is operatively associated with the promoter. The coding sequence may encode a polypeptide and/or a functional RNA. Typically, a "promoter" refers to a nucleotide sequence that contains a binding site for RNA polymerase II ("core promoter" herein) and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) Annu. Rev. Biochem. 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

A "core promoter" as known in the art is a short DNA sequence comprised of a TATA box and/or other DNA elements that serve to recruit general transcription factors and RNA polymerase and specify the site of transcription initiation, to which regulatory elements may be added for control of expression. The core promoter is also referred to as a "minimal promoter" because it is functional on its own to promote a basal level of transcription (and "core promoter" and "minimal promoter" are used interchangeably herein). A core promoter thus consists only of basal elements needed for transcription initiation, e.g., a TATA box and/or an Initiator element.

A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid. In some embodiments, promoters useful with the constructs of the invention may be any combination of heterologous and/or endogenous promoters.

By "operably linked" or "operably associated" as used herein, it is meant that the indicated elements are functionally related to each other, and are also generally physically related or associated. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence of interest if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

In the present invention, the EBS (e.g., of Formula I) may be provided as a distal-proximal promotor or element that is operatively associated with a "core promoter" that recruits RNA Pol II and basal transcription factors (TFs). As known in the art, distal and proximal promoters have sequences that recruit gene- or tissue-specific TFs (such as EIN3 in the case of EBSnew) that, in turn, help bring RNA Pol II and basal TFs to the promoter. In some embodiments, the 35S core promoter (−46 to +8) is used, although any core promoter can be used, including synthetic and viral minimal promoters such as FMV from Figwort mosaic virus. See, e.g., Kumar et al. (2012) Development of a salicylic acid inducible minimal sub-genomic transcript promoter from Figwort mosaic virus with enhanced root- and leaf-activity using TGACG motif rearrangement. *Gene* 503 (1), 36-47.

"Nucleotide sequence of interest," "nucleic acid of interest," and "polynucleotide of interest" are used interchangeably herein and refer to any polynucleotide sequence which, when introduced into an organism such as a plant, confers upon the organism a desired characteristic such as detection of expression of a marker (or "reporter") protein, tolerance to abiotic stress, antibiotic resistance, virus resistance, insect resistance, disease resistance, or resistance to other pests, herbicide tolerance, improved nutritional value, improved performance in an industrial process, or altered reproductive capability. The nucleotide sequence of interest may also be one that is useful for the production of commercially valuable products such as enzymes or metabolites in the plant. The nucleotide sequence of interest can also encode a polypeptide and/or an inhibitory polynucleotide (e.g., a functional RNA).

By the term "express," "expressing" or "expression" (or other grammatical variants) of a nucleic acid coding sequence, it is meant that the sequence is transcribed. In particular embodiments, the terms "express," "expressing" or "expression" (or other grammatical variants) can refer to both transcription and translation to produce an encoded polypeptide.

The term "abiotic stress" as used herein refers to outside, nonliving, factors which can cause harmful effects to plants. Thus, as used herein, abiotic stress includes, but is not limited to, drought/dehydration, and/or rehydration, or cycles of dehydration and rehydration. Parameters for the abiotic stress factors are species specific and even variety specific and therefore vary widely according to the species/variety exposed to the abiotic stress. In addition, because most crops are exposed to multiple abiotic stresses at one time, the interaction between the stresses affects the response of the plant. Thus, the particular parameters for high/low temperature, light intensity, drought and the like, which impact crop productivity, will vary with species, variety, degree of acclimatization and the exposure to a combination of environmental conditions.

The nucleotide sequence of interest in some embodiments may encode an antioxidant protein. Examples of antioxidant proteins include, but are not limited to, catalases, glutathione peroxidases, and superoxide dismutases such as manganese superoxide dismutase (MnSOD). See, e.g., U.S. Pat. No. 7,994,406 to Patell. Antioxidant proteins may also include enzymes involved in the biosynthesis of antioxidant compounds such as vitamins (Vitamin C, Vitamin B6), flavonoids (e.g., anthocyanidins), lycopene, etc.

Reporter proteins that may be encoded by a nucleic acid of interest include, but are not limited to, fluorescent or luminescent proteins or enzymes such as green fluorescent protein, luciferase, β-glucuronidase (GUS), mCherry, mTagBFP2, Cerulean, Ypet, Ruby, etc. See, e.g., U.S. Pat. No. 6,232,107 to Bryan et al.

In some embodiments, a recombinant nucleic acid construct of the invention may be an "expression cassette" or may be comprised within an expression cassette. As used herein, "expression cassette" means a recombinant nucleic acid construct comprising a polynucleotide of interest, wherein said polynucleotide of interest is operably associated with at least one control sequence (e.g., a promoter).

An expression cassette may also optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked polynucleotide of interest, may be native to the host cell, or may be derived from another source (i.e., foreign or heterologous to the promoter, to the polynucleotide of interest, to the host, or any combination thereof).

An expression cassette (e.g., recombinant nucleic acid constructs and the like) may include a nucleotide sequence of interest that is a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Of course, many examples of suitable selectable markers are known in the art and can be used in the expression cassettes described herein.

As a non-limiting example, the expression cassette may comprise, from 5' to 3', the EBS as taught herein (e.g., pEBSnew), a minimal promotor (e.g., 35S minimal promoter), a nucleic acid of interest (e.g., BT delta endotoxin coding sequence), and a transcriptional terminator (e.g., NOS terminator). Such an expression cassette may be used to induce the BT toxin in response to ethylene produced by the plant tissues attached by an herbivore insect.

In addition to expression cassettes, the nucleic acid construct and nucleotide sequences described herein may be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. A vector can transform a host cell either by integration into the cellular genome, or it may exist extra-chromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). A nucleic acid construct in the vector may be under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the recombinant nucleic acid constructs of this invention and/or expression cassettes comprising the recombinant nucleic acid constructs of this invention may be provided in vectors as described herein and as known in the art.

The terms "transformation," "transfection," and "transduction" as used herein refer to the introduction of a heterologous nucleic acid into a cell. Such introduction into a cell may be stable or transient. Thus, in some embodiments, a host cell or host organism is stably transformed with a nucleic acid construct of the invention. In other embodiments, a host cell or host organism is transiently transformed with a recombinant nucleic acid construct of the invention.

As used herein, the term "stably introduced" means that the introduced polynucleotide is stably incorporated into the genome of the cell, and thus the cell is stably transformed with the polynucleotide. When a nucleic acid construct is stably transformed and therefore integrated into a cell, the integrated nucleic acid construct is capable of being inherited by the progeny thereof, more particularly, by the progeny of multiple successive generations.

"Transient transformation" in the context of a polynucleotide means that a polynucleotide is introduced into the cell and does not integrate into the genome of the cell.

Transient transformation may be detected by, for example, an enzyme-linked immunosorbent assay (ELISA) or western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant, a mammal, an insect, an archaea, a bacterium, and the like). Stable transformation of a cell can be detected by, for example, a northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

A recombinant nucleic acid construct of the invention can be introduced into a cell by any method known to those of skill in the art. Exemplary methods of transformation or transfection include biological methods using viruses and bacteria (e.g., *Agrobacterium*), physicochemical methods such as electroporation, floral dip methods, particle or ballistic bombardment, microinjection, whiskers technology, pollen tube transformation, calcium-phosphate-mediated transformation, nanoparticle-mediated transformation, polymer-mediated transformation including cyclodextrin-mediated and polyethyleneglycol-mediated transformation, sonication, infiltration, as well as any other electrical, chemical, physical (mechanical) and/or biological mechanism that results in the introduction of nucleic acid into a cell, including any combination thereof.

In some embodiments of the invention, transformation of a cell comprises nuclear transformation. In still further embodiments, the recombinant nucleic acid construct of the invention can be introduced into a cell via conventional breeding techniques.

The invention further provides a recombinant plant cell or plant organism comprising the recombinant nucleic acid constructs taught herein, and/or comprising the recombinant expression cassette, plasmid, or otherwise containing a recombinant nucleic acid constructs of the invention.

As used herein, the terms "transformed" and "transgenic" refer to any plant, plant cell, plant tissue (including callus), or plant part that contains all or part of at least one recombinant or isolated nucleic acid, polynucleotide or nucleotide sequence. In representative embodiments, the recombinant or isolated nucleic acid, polynucleotide or nucleotide sequence is stably integrated into the genome of the plant (e.g., into a chromosome or as a stable extra-chromosomal element), so that it is passed on to subsequent generations of the cell or plant.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs plant cell tissue cultures, plant calli, plant clumps, and the like. As used herein, "shoot" refers to the above ground parts including the leaves and stems.

The term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ.

Any plant (or groupings of plants, for example, into a genus or higher order classification) can be employed in practicing the present invention including angiosperms and/or gymnosperms, monocots and/or dicots.

Exemplary plants include, but are not limited to, corn (*Zea mays*), canola (*Brassica napus, Brassica rapa* ssp.), alfalfa (*Medicago saliva*), rice (*Oryza sativa*, including without limitation Indica and/or *Japonica* varieties), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tobacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lemna*), oats (*Avena sativa*), barley (*Hordium vulgare*), vegetables, ornamentals, conifers, and turfgrasses (e.g., for ornamental, recreational or forage purposes), and biomass grasses (e.g., switchgrass and *Miscanthus*).

Vegetables include Solanaceous species (e.g., tomatoes; *Lycopersicon esculentum*), lettuce (e.g., *Lactuea sativa*), carrots (*Caucus carota*), cauliflower (*Brassica oleracea*), celery (*Apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (C. Hubbard), Butternut squash (*C. moschata*), Zucchini (*C. pepo*), Crookneck squash (C. crookneck), *C. argyrosperma, C. argyrosperma* ssp. *sororia, C. digitata, C. ecuadorensis, C. foetidissima, C. lundelliana,* and *C. martinezii*, and members of the genus *Cucumis* such as cucumber (*Cucumis sativus*), cantaloupe (*C. cantalupensis*), and musk melon (*C. melo*).

Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and *chrysanthemum*.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass include but are not limited to *zoysia* grass, bent grass, fescue grass, bluegrass, St. Augustine grass, Bermuda grass, buffalo grass, rye grass, and orchard grass.

Also included are plants that serve primarily as laboratory models, e.g., *Arabidopsis*.

Ethylene Binding Sequences (EBS) and Uses Thereof

Provided herein are ethylene binding sequences (EBS) useful to drive gene expression in response to ethylene. The EBS may be an "inverted repeat" of coreEBS-like sequences with a 1-bp overlap ("2EBS(-1)") as described herein. The "inverted repeat" need not be the exact sequence in an inverted form, so long as the basic 2EBS(-1) structure as taught herein is present (see FIG. 1, Panel A).

Such EBS may be a sequence of Formula I (SEQ ID NO:48):

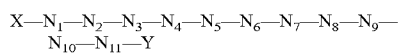

wherein:
$N_1$ is A or G;
$N_2$ is T;
$N_3$ is G, T or A;
$N_4$ is C;
$N_5$ is A;
$N_6$ is A or T;
$N_7$ is T;
$N_8$ is G;
$N_9$ is A, T or C;
$N_{10}$ is A;
$N_{11}$ is T or C; and
X and Y are each independently present or absent and when present is each independently a spacer sequence, which may be comprised of any combination of 2, 5, or 10, to 20, 30 or 50 nucleotides. In some embodiments, the spacer may be 2 to 10 nucleotides, or 4 to 8 nucleotides (e.g., 5 nucleotides).

In some embodiments, the spacer sequence does not comprise another transcription factor binding element. As a non-limiting example, the consensus binding site for cytokinin activated transcription, 5'-(A/G)GAT(C/T)T-3', may be removed from the spacer sequence (Plant Physiol. 2013 March; 161(3): 1066-1075.). See also: agris-knowledgebase.org/AtcisDB/bindingsites.html.

Examples of preferred sequences of Formula I include, but are not limited to, those listed in Table 1, with key (conserved) bases capitalized (see also FIG. 1, Panel A).

TABLE 1

Example 2EBS(-1) of Formula I

| Formula I Example Sequences | |
|---|---|
| X-ATgCAaTGaAT-Y | SEQ ID NO: 1 |
| X-GTtCAaTGaAT-Y | SEQ ID NO: 2 |
| X-GTgCAaTGtAT-Y | SEQ ID NO: 3 |
| X-ATaCAtTGaAC-Y | SEQ ID NO: 4 |
| X-ATaCAtTGaAT-Y | SEQ ID NO: 5 |
| X-ATaCAtTGtAT-Y | SEQ ID NO: 6 |
| X-ATaCAaTGcAT-Y | SEQ ID NO: 7 |
| X-ATaCAaTGtAT-Y | SEQ ID NO: 8 |
| X-ATtCAaTGcAT-Y | SEQ ID NO: 9 |
| X-ATtCAaTGaAC-Y | SEQ ID NO: 10 |
| X-ATtCAtTGcAC-Y | SEQ ID NO: 11 | wherein X and Y are as defined above.

The EBS may be provided as a combination, or "stack," of two or more EBS of Formula I directly adjacent to each other (e.g., 2, 3, 4, 5, 6, 7, 8, 9, 10, 11, or 12 or more EBS). In some embodiments, the two or more EBS may comprise EBS of Formula I which are not identical with one another (e.g., 2, 3, 4, 5, 6, 7, 8, 9, 10, 11, or 12 or more different EBS in the stack, which may also optionally include one or more duplicate EBS, and optionally up to 50, 75 or 100 EBS of Formula I).

The EBS may be operably linked to a core promoter to drive ethylene-dependent expression of an operatively associated nucleic acid of interest. In some embodiments, the core promoter may be within 0 to 2,000 base pairs downstream (3') of the EBS. In some embodiments, the EBS may be inserted into the sequence of a full promoter, upstream of the core promoter sequence of that promoter.

In some embodiments, the EBS of Formula I does not comprise another transcription factor binding element, or does comprise another transcription binding element, as desired. For example, the sequence of the stacked EBS may be modified to remove or add such sequences, particularly at the X and Y linker positions. See, e.g.: agris-knowledge-base.org/AtcisDB/bindingsites.html. For example, a GCC box recognized by a subset of ERF transcription factors can be introduced at junctions between EBS copies to make the ethylene-responsive promoter also inducible by ERFs. See, e.g., Hao et al. (1998) Unique Mode of GCC Box Recognition by the DNA-binding Domain of Ethylene-responsive Element-binding Factor (ERF Domain) in Plant, *J. Biol. Chem.* vol. 273, no. 41, 26857-26861.

In some embodiments, stacked EBS of Formula I may be selected from the group consisting of SEQ ID NOS:14 and 27-26; and sequences with 90, 92, 95 or 97% identity thereto.

The EBS may be used in an expression cassette comprising the EBS and core promoter operably linked to a nucleic acid of interest. In some embodiments, the nucleic acid of interest encodes a reporter protein, such as those listed above. Nucleic acids of interest may also include those encoding a toxin (e.g., Barnase, see Faden et al. (2019) Modulating Protein Stability to Switch Toxic Protein Function On and Off in Living Cells, *Plant Physiol* vol. 179, 929-942) to arrest plant growth or kill a plant, a vitamin-biosynthesis protein to make a valuable nutrient (e.g., PDX1.1 to increase vitamin B6 levels, see Mangel et al. (2019) Enhancement of vitamin B6 levels in rice expression *Arabidopsis* vitamin B6 biosynthesis de novo genes, The Plant Journal vol. 99, 1047-1065), a pigment protein (e.g., synthetic protein Ruby, see He et al. (2020) A reporter for noninvasively monitoring gene expression and plant transformation, *Horticulture Research* 7, no. 152) to change the plant or organ color, a pathogen defense protein (e.g., NPR1, see Cao et al. (1998) Generation of broad-spectrum disease resistance by overexpression of an essential regulatory gene in systemic acquired resistance, *PNAS* vol. 95, no. 11, 6531-6536) to make plant withstand a pathogen attack, a flavor inducing enzyme (e.g., AADCla, see Tieman et al. (2006) Tomato aromatic amino acid decarboxylases participate in synthesis of the flavor volatiles 2-phenylethanol and 2-phenylacetaldehyde, *PNAS* vol. 103, no. 21, 8287-8292) or a sweet-tasting protein (e.g., Monellin, see Reddy et al. (2015) Improving Flavour and Quality of Tomatoes by Expression of Synthetic Gene Encoding Sweet Protein Monellin, *Mol. Biotech.* vol. 57, 448-453) to modify the fruit or vegetable taste, an insect toxin (e.g., BT delta endotoxin), etc.

The construct comprising an EBS as taught herein may be introduced into a plant cell to produce a transformed plant cell by standard methods known in the art. The plant cell may be regenerated into a transformed plant, and the transformed plant, or a plant part, or plant cell therefrom, may be exposed to ethylene (e.g., by applying ethylene or an ethylene precursor 1-aminocyclopropane-1-carboxylic acid (ACC)), thereby inducing expression of a nucleic acid of interest operably linked to the EBS. Depending on the method of transformation used, a recombinant nucleic acid construct comprising the EBS may be integrated into the genome of the plant, or not integrated into the genome of the plant.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1: An Inverted Repeat of coreEBS with the Overlap of the Motifs Predicts EIN3 Binding in *Arabidopsis* Genome More Specifically than Other EBS

*Arabidopsis thaliana* reporter EBS:GUS driven by the EIN3 binding site (Stepanova et al., 2007) is widely used as a sensor for detection of ethylene signaling. The binding specificities of *A. thaliana* EIN3 and its homolog from *Nicotiana tabacum*, TOBACCO EIN3-LIKE (TEIL), were investigated using high-throughput in vitro binding assays such as systematic evolution of ligands by exponential enrichment (SELEX) (Kosugi and Ohashi, 2000), chromatin immunoprecipitation and sequencing (ChIP-seq), protein binding microarrays (PBM) (Chang et al., 2013), and DNA affinity purification and sequencing (DAP-seq) (O'Malley et al., 2016). The corresponding models share a common 6-bp core sequence (hereinafter referred to as coreEBS).

We first investigated EIN3 binding preferences at the genome level using publicly available ChIP-seq data on EIN3 binding in three-day-old etiolated *Arabidopsis* seedlings treated with ethylene gas for four hours (Chang et al., 2013, Temporal transcriptional response to ethylene gas drives growth hormone cross-regulation in *Arabidopsis*. *Elife* 2, e00675). We initially focused on ChIP-seq rather than on published DAP-seq data (O'Malley et al., 2016, Cistrome and Epicistrome Features Shape the Regulatory DNA Landscape. *Cell* 165, 1280-1292) to ensure that we capture the sequences associated with the EIN3 function in vivo. De novo motif search in the peaks with Homer tool (Heinz et al., 2010, Simple combinations of lineage-determining transcription factors prime cis-regulatory elements required for macrophage and b cell identities. *Mol. Cell* 38, 576-589) discovered a previously unknown EBS architecture top ranked among the enriched motifs (p-value 1e-300).

This new configuration, referred to as 2EBS(−1), is a head-to-head inverted repeat of coreEBS-like sequences with a 1-bp overlap (FIG. 1, Panel A). The motifs with a single coreEBS copy, designated TEIL-like and GC-EBS, were enriched in ChIP-seq peaks to a much lower extent, with p-values of 1e-15 and 1e-14, respectively. TEIL-like sequence is the most similar to the TEIL binding site identified in the aforementioned SELEX experiment in tobacco (Kosugi and Ohashi, 2000, Cloning and DNA-binding properties of a tobacco Ethylene-Insensitive3 (EIN3) homolog. *Nucleic Acids Res.* 28, 960-967), whereas GC-EBS is the closest to the EIN3 target site found in the ERF1 and EDF1 through 4 gene promoters (Solano et al., 1998, Nuclear events in ethylene signaling: a transcriptional cascade mediated by ETHYLENE-INSENSITIVE3 and ETHYLENE-RESPONSE-FACTOR1. *Genes Dev.* 12, 3703-3714; Stepanova, 2007, Multilevel interactions between ethylene and auxin in *Arabidopsis* roots. *Plant Cell* 19, 2169-2185).

The predominant role of the new 2EBS(−1) repeat in EIN3 binding was further supported by the quantitative analysis of 2EBS(−1), TEIL-like and GC-EBS occurrence in ChIP-seq peaks relative to that in the whole-genome set of gene promoters. 2EBS(-1) repeat showed greater occurrence in EIN3-bound ChIP-seq peaks as compared to the motifs with a single coreEBS at low false-positive rates (FIG. 1, Panel B).

Next, we tested if preferential binding of EIN3 to 2EBS (-1) could be caused by chromatin organization. Since DAP-seq detects TF interactions with naked chromosomal DNA, we repeated de novo motif search in EIN3 DAP-seq data from *Arabidopsis* (O'Malley et al., 2016). In DAP-seq peaks, 2EBS(-1) enrichment was again top ranked (p-value 1e-659). Therefore, the 2EBS(-1) repeat rather than the previously identified single-coreEBS-containing motifs is the primary EIN3 binding site in the *Arabidopsis* genome.

The finding that the tandem arrangement of two adjacent copies of EBS improves EIN3 binding to DNA is in agreement with the previously reported EIN3 tendency to bind DNA as a homodimer (Solano et al., 1998, Nuclear events in ethylene signaling: a transcriptional cascade mediated by ETHYLENE-INSENSITIVE3 and ETHYLENE-RESPONSE-FACTOR1. *Genes Dev.* 12, 3703-3714; Song et al., 2015, Biochemical and Structural Insights into the Mechanism of DNA Recognition by *Arabidopsis* ETHYLENE INSENSITIVE3. *PLoS One* 10, e0137439). Accordingly, recent fine-scale in vitro gel-shift experiments demonstrated that head-to-head inverted repeats of coreEBS-like sequences (ATGTAT or ATGTAC) separated by a 8-15 bp spacer display greater affinity for EIN3 than the DNA substrates with a single coreEBS sequence (Song et al., 2015). Therefore, we explored what configurations of the two head-to-head coreEBS repeats besides 2EBS(-1) could be critical for EIN3 binding on a genome-wide scale. We analyzed the occupancy of EBS repeats with different architecture (in terms of mutual orientation of coreEBS motifs and spacer length) in ChIP-seq peaks using MCOT algorithm (Levitsky et al., 2019, A single ChIP-seq dataset is sufficient for comprehensive analysis of motifs co-occurrence with MCOT package. *Nucleic Acids Res.* 47, e139).

Figure 2:
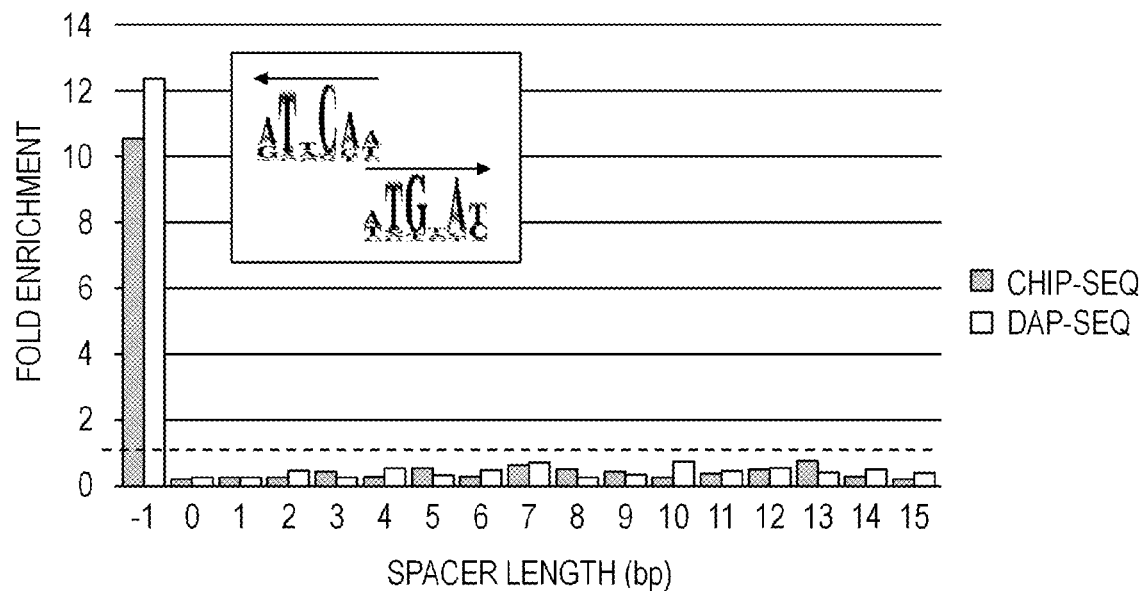
FIG. 2. The occurrence of coreEBS head-to-head inverted repeats in EIN3 binding regions compared to random expectation. ChIP-seq and DAP-seq peaks were used as EIN3 binding regions. A random background dataset was generated for comparison and the frequencies of occurrence of coreEBS inverted repeats were estimated in EIN3 DNA binding data and in the background dataset using MCOT algorithm (Levitsky et al., 2019, A single ChIP-seq dataset is sufficient for comprehensive analysis of motifs co-occurrence with MCOT package. *Nucleic Acids Res.* 47, e139). Fold enrichment is the ratio of the ChIP-seq or DAP-seq frequencies relative to that of the background dataset. Dotted line denotes randomly expected fold enrichment. The logo represents configuration of the enriched repeat. Arrows designate coreEBS sequences.

To our surprise, head-to-head inverted repeats of coreEBS with 8-15 bp spacers were not enriched in ChIP-seq peaks compared to random expectation, and neither were the other configurations of two EBS repeats, except for 2EBS(-1), as shown in FIG. 2. Moreover, we observed a similar occurrence profile for dual coreEBS repeats in DAP-seq data, pinpointing 2EBS(-1) as the most likely candidate for the canonical EIN3 homodimer binding site and downplaying the possible role of other dual coreEBS configurations in EIN3 recruitment.

Since our bioinformatic analysis identified the 2EBS(-1) sequence as the canonical EIN3 binding site, we hypothesized that it should predominate in EIN3-binding datasets across all data points. We therefore analyzed whether this DNA element is associated with a sustained profile of EIN3 binding, i.e., recruits EIN3 regardless of the duration of ethylene treatment. We preprocessed three previously published EIN3 ChIP-seq datasets from three-day-old etiolated *Arabidopsis* seedlings that were treated with ethylene gas for one, four and 12 hours (Chang et al., 2013) and intersected the corresponding EIN3-binding peaks. The peaks that overlapped between all three datasets were classified as the sustained EIN3-binding events. To differentiate between distinct EBS configurations (2EBS(-1), TEIL-like and GC-EBS), we kept only the peaks harboring one type of EBS for further analysis and discarded the peaks with combinations of these elements. We estimated the associations of distinct EBS configurations with sustained EIN3 binding using Fisher's exact test.

Figure 3:
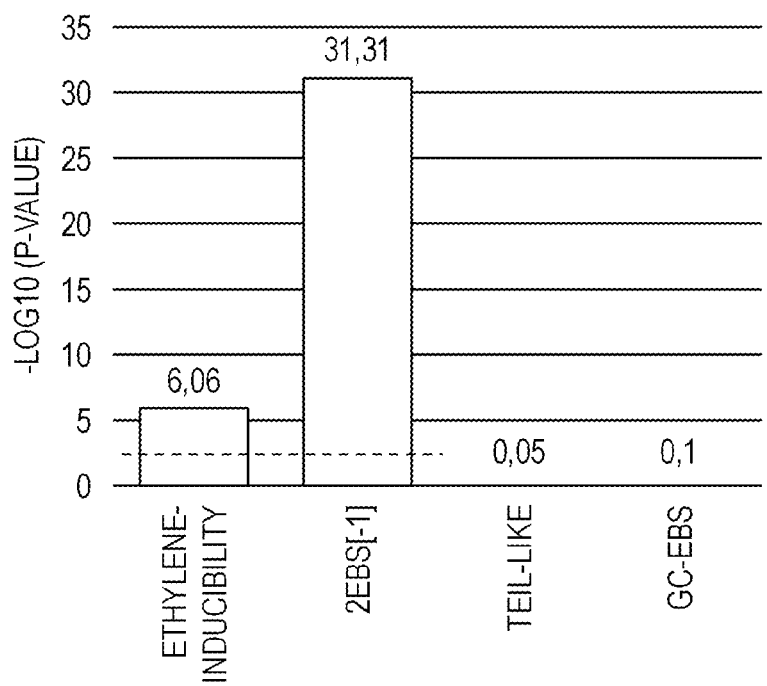
FIG. 3. Association of different gene features with sustained EIN3 binding in ChIP-seq. The dashed line designates the threshold of -log 10(0.05/4)=1.90.

Consistent with our expectations, 2EBS(-1) repeat was significantly associated with sustained EIN3 binding (p-value 4.9e-32), whereas the single-coreEBS motifs, TEIL-like and GC-EBS, were not (FIG. 3).

We next evaluated the correlation between sustained EIN3 binding and gene responsiveness to ethylene in a set of EIN3 targets identified based on ChIP-seq data. For further analysis, we again kept only the genes harboring one type of EBS in the corresponding EIN3-bound sequences. To characterize ethylene responsiveness, we preprocessed three previously published RNA-seq datasets for three-day-old etiolated *Arabidopsis* seedlings treated with ethylene gas for one, four and 12 hours, or left untreated (Chang et al., 2013). We considered the gene ethylene responsive if it was differentially expressed in at least one dataset.

We found that sustained EIN3 binding to a gene promoter was significantly associated with the gene's activation in response to ethylene treatment (p-value 1.3e-08) (FIG. 3). Taken together, our results suggest that of all EBS configurations under study, 2EBS(-1) likely prevails in ensuring a substantial part of EIN3-mediated responses to ethylene.

Example 2: A New Genetic Sensor for Highly Sensitive Detection of Ethylene Signaling in *Arabidopsis*

In the only available synthetic ethylene reporter EBS: GUS (Stepanova et al., 2007), the reporter gene is driven by a tandem of single-core EBS-containing GC-EBS motifs (Stepanova, 2001). In light of the bioinformatic data reported above, we hypothesized that 2EBS(-1) should induce more a pronounced response to ethylene than EBS: GUS.

Figure 4:
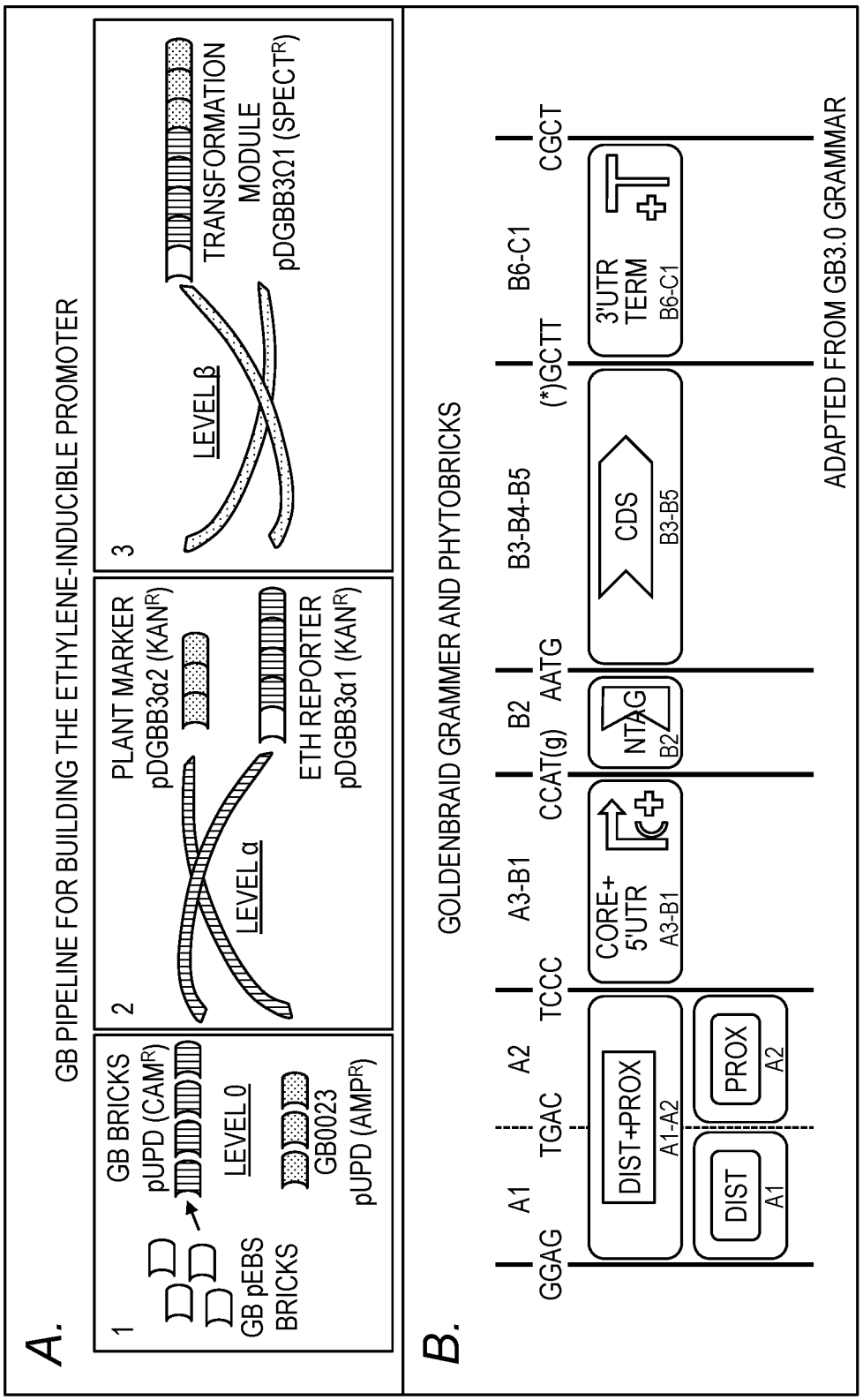
FIG. 4. GB phytobricks used to build the different ethylene-inducible reporters. Synthetized ethylene promoters were domesticated in pUPD2 (Panel A, 1) following the GB grammar rules for a combined distal-proximal promoter or for separate distal and proximal promoter bricks (Panel B). The new promoter bricks were assembled into TUs in combination with other pre-made bricks (Panel A, 1, and see also Panel B for grammar information) using the level alpha of the GB multiplexing technology (Panel A, 2). Each of the four promoters was combined with a fluorescent (Panel C) and a GUS-containing (Panel D) reporter. In parallel, the TU containing the Bar gene conferring resistance to the BASTA herbicide (GB0023 stock, Panel A, 1) was also moved into the level alpha vector (Panel A, 2). Finally, each ethylene-inducible transcriptional reporter was assembled with the plant selectable marker unit into a transformation module (Panel E) following the binary rules of GB assemblies in the level omega plasmid (Panel A, 3). The bricks in this figure include four ethylene-specific promoters (pEBSnew (GB A1-A2), pmutantEBSnew (GB A1-A2), pEBSclassic (GB A1-A2), pEBS-S10 (GB A1) and pEBS-S10 (GB A2)); a 35S minimal core promoter (-46), 35Smp0 (GB A3-B1); three nuclear localization signal tags harboring three different nucleotide variants, NLSv1, NLSv2 and NLSv3 (GB B2) (unpublished data); two reporter genes (the YPet CDS repeated three times or β-glucoronidase CDS (GB B3-B4-B5)); and a 35S terminator, 35سterm0 (GB B6-C1). Additional information about the vectors used in every level of assembly and their selectable marker resistance is also provided in Panel A. Images were adapted from GB3.0 grammar.
Figure 4:
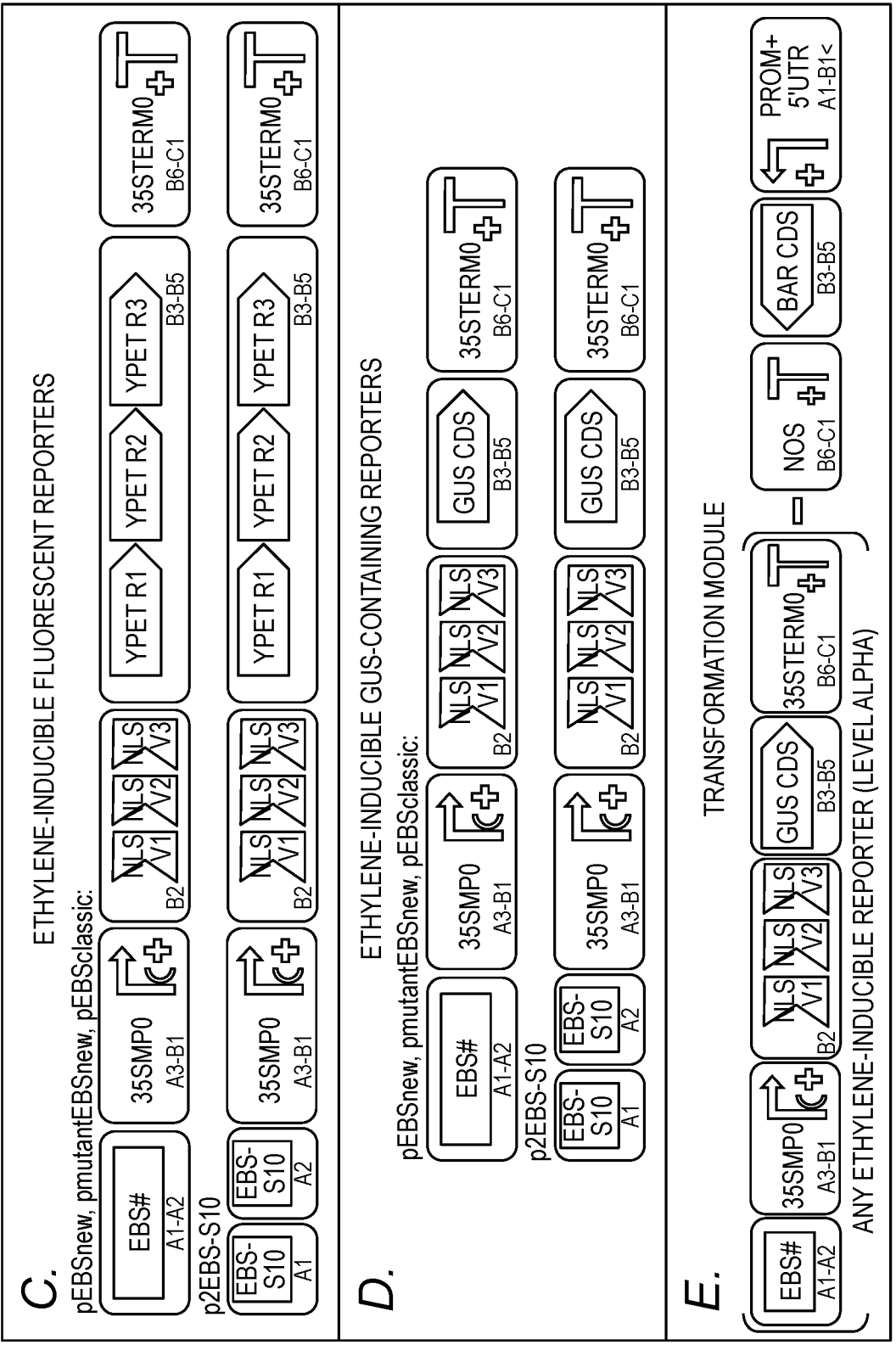

The synthetic ethylene transcriptional reporters described in this work were built using the GoldenBraid (GB) multiplexing technology (Sarrion-Perdigones et al., 2011 and 2013; Vazquez-Vilar et al., 2017). Each ethylene-specific distal promoter was domesticated into the GB platform (Level 0) in the pUPD2 vector by following the flanking 4-nucleotide coding grammar rules for a distal and proximal promoter bricks (aka A1-A2, GGAG-TCCC) (see FIG. 4, Panels A-B). The new synthetic ethylene bricks were assembled individually into two different transcriptional units (TUs) to create ethylene-inducible reporters (Level Alpha) in pDGBB3alpha1 and pDGBB3alpha2 vectors (FIG. 4, Panels C-D). The final step was to assemble the TUs into a transformation-ready module together with a plant selectable marker (Level Omega) in pDGBB3omega1 (FIG. 4, Panel E). The design of all the sequences described below was performed in silico using the Benchling online platform (Benchling, San Francisco, California) prior to their synthesis and assembly.

Four synthetic ethylene-specific promoters were tested: the 2EBS[-1]-containing 10xEBSn ("n" for "new") generated in this work, the mutant version of 10xEBSn (10xmutEBSn) also from this work, a stacked version of the original 5xEBS (Stepanova, 2001) referred herein as 10xEBSc ("c" for "classic"), which differs from the original construct by having ten repeats of EBSc spaced by 10 nucleotides as compared to five repeats spaced by 3 nucleotides (Stepanova and Ecker, unpublished data), and a 10-copy tandem of the previously reported sequence 2EBS-S10 (Song et al., 2015). These promoters are listed in Table 2.

TABLE 2

| Promoter | Transcription Factor Binding Element (TFBE) | Size (TFBE) | SEQ ID NO | Source | Reference |
|---|---|---|---|---|---|
| EBS classic (x10) | (AGCCTCATGATCAAAGGGGGATG CACTATTTAAGGATCT)x10 | 400(40)bp | SEQ ID NO: 12 | EDF1-Ethylene Response DNA-binding Factors | This project |
| 2 EBS-S10 (x10) | (AAGATACATGCAAAAAAGCATGTAT CTT)x10 | 280(28)bp | SEQ ID NO: 13 | Synthetic | Song et al., 2015 (PLoS ONE) |
| EBSnew (x10) | gtatcatgcaatgaatcaAcc\|tcttggttcaat gaatcgagt\|Gcaatatacattgtattatgg\| gatGgattcaatgcatCgttc\|tctcaattcatt gcactcTta\|tttaaatacaatgcatcaGta\| gtccgattcattgcacaacGa\|attggatacaa tgtatttgtG\|aacagatacattgaacattag\| gagaGatacattgaatctata | 210(21)bp | SEQ ID NO: 14 | Synthetic | This project |
| mutEBSnew (x10) | gtatcaggcaatgactcaAcc\|tcttggttgaa cgaatcgagt\|Gcaatatagattgtaatatgg\| gatGgattaaacgcatCgttc\|tctcaattcgt agcactcTta\|tttaaatactaggcatcaGta\| gtccgattccttgctcaacGa\|attggctacaat gtaattgtG\|aacagatagatagaacattag\| gagaGctacattgaaactata | 210(21)bp | SEQ ID NO: 15 | Synthetic | This project |
| EBSoriginal (x5) | (CCTCATGATCAAAGGGGGATGCA CTATTTAAGAT)x5 | 173(35)bp | SEQ ID NO: 16 | EDF1-Ethylene Response DNA-binding Factors | Stepanova et al., 2007 (Plant Cell) |

These synthetic promoters were initially screened for forbidden BsaI and BsmBI restriction sites within their sequences to allow their domestication into the GB platform. Then, the 4-nucleotide coding grammar corresponding to a distal-proximal promoter brick (A1-A2) was added to their sequences: the GGAG code at the 5' end, and the TCCC code at the 3' end. In addition, to be cloned into the GB Level 0 plasmid pUPD2, these GB codes were flanked by additional DNA sequences: (1) two pUPD2-compatible 4-nucleotide codes, one upstream of the GB A1 code (CTCG at the 5' end) and another downstream of the GB A2 code (TGAG at the 3' end); and (2) two flanking restriction sites for the type IIS enzyme BsmBI (nnnnCGTCTCn; SEQ ID NO:47) upstream and downstream of the aforementioned pUPD2 codes. Due to DNA synthesis limitations, these extra DNA sequences were not included in the synthetized sequences and were incorporated into the DNA fragments via PCR primers. The promoter sequences were too short to use the GB domestication tool, so the aforementioned flanks were added manually to the sequences of interest.

Because the highly repetitive nature of the 2EBS-S10 promoter made the GB domestication and commercial synthesis impossible, the constructs were made by generating repetitive promoters that involved synthesizing the desired sequences with spacers that were enzymatically removed during subcloning into pUPD2. As a result, half of the 2EBS-S10 promoter was domesticated independently using the grammar for the distal promoter A1 brick (5'-GGAG and TGAC-3') and the other half using the grammar for the proximal A2 promoter brick (5'-TGAC and TCCC-3') (FIG. 4, Panel B). Once the grammar codes were incorporated into the ethylene-inducible promoter bricks in silico, commercial synthesis was performed by IDT in the form of DNA gBlocks.

Synthetized promoters were amplified using iPROOF™ High-Fidelity DNA Polymerase (Bio-Rad®), chloroform-purified and stored at −20° C. until use. The fragments containing the promoter sequences and their GB overhangs were cloned into the pUPD2 entry vector following the GB instructions (Sarrion-Perdigones, et al., 2014; Vazquez-Vilar, et al., 2015) with some modifications: the digestion-ligation cycle started with an initial BsmBI (NEB) digestion step at 55° C. for 20 min, followed by the addition of the DNA T4 ligase (NEB) prior to the full GB cycle (4 min at 37° C. and 5 min at 16° C., 25 times) and a final digestion step at 55° C. for 20 min with freshly added BsmBI and the inactivation of both enzymes at 80° C. for 20 min. The reactions were transformed into homemade chemically competent E. coli TOP10 cells (ThermoFisher) and the transformed colonies were selected in LB Agar (Genessee Scientific) supplemented with chloramphenicol (25 μL mg$^{-1}$) (GoldBio) and X-Gal (20 μL mg$^{-1}$) (GoldBio). Plasmid DNA from white colonies was extracted using alkaline lysis, verified by restriction digest and Sanger sequencing, and stored at −20° C.

Confirmed pUPD2 plasmids containing the distal-proximal ethylene-inducible promoters (A1-A2 grammar) were assembled into the destination vector pDGB3alpha1 along with the following GB bricks harbored in pUPD2: a −46 minimal 35S promoter (A3-B1), a triple nuclear localization signal (3×NLS, B2), a triple yellow fluorescent protein (3×YPet) or a β-Glucoronidase CDS (GUS) (B3-B5), and the 35S terminator (B6-C1 grammar) to build two different types of transcriptional reporters (FIG. 4, Panels C-D). These pUPD2 DNA parts were built previously in our lab following the aforementioned modified GB protocol. The assemblies in pDGB3alpha1 were done following the GB guidelines (Sarrion-Perdigones, et al., 2014; Vazquez-Vilar, et al., 2015) with some modifications: the digestion-ligation cycle (4 min at 37° C. and 5 min at 16° C., repeated 25 times) was followed by a final digestion step at 37° C. for 20 min and a 20-min enzyme inactivation step at 65° C. The digestion in pDGB3alpha1 was done with BsaI (NEB) at 37° C. The reaction products where then transformed into homemade Top10 cells and selected in LB Agar supplemented with kanamycin (50 µg mL$^{-1}$) (GoldBio) and X-Gal (20 µL mg$^{-1}$), with white colonies tested as described above for pUPD2 constructs. In parallel, the GB0023 stock from the GB stock collection harboring a TU for the plant selectable marker Bar that confers resistance to the BASTA herbicide (Murakami et al., 1986) was moved from the Level 0 plasmid pUPD to the Level alpha vector pDGB3alpha2 following the procedure described above for cloning other TUs in pDGB3alpha1.

The pDGB3alpha1 plasmids harboring the ethylene-inducible reporters were assembled together with the plant BASTA resistance marker Bar harbored in pDGB3alpha2 into the pDGB3omega1 vector following the GB binary assembly rules (Sarrion-Perdigones, et al., 2014; Vazquez-Vilar, et al., 2015) with some modifications. The digestion-ligation cycle (4 min at 37° C. and 5 min at 16° C., repeated 25 times) was followed by a final digestion step at 55° C. for 20 min and a 20-min enzyme inactivation step at 80° C. The reactions were transformed into Top10 cells and selected in LB Agar supplemented with spectinomicin (100 µg mL$^{-1}$) (GoldBio) and X-Gal (20 µL mg$^{-1}$), with white colonies tested as described above for pUPD2 and pDGB3alpha1 constructs.

Both the ethylene inducible reporters (level alpha) and the final modules (level omega) were transformed into *Agrobacterium tumefaciens* strain GV3101 by electroporation (Gene Pulser, Bio-Rad®) as described (Alonso and Stepanova, 2015; Shen and Forde, 1989). Positive colonies were identified in LB Agar (Genessee Scientific) supplemented with spectinomicin (100 µg mL$^{-1}$) (Gold Biotechnology), rifampicin (20 µg mL$^{-1}$) (Gold Biotechnology) and gentamycin (25 µg mL$^{-1}$) (Gold Biotechnology), re-streaked once, grown at 28° C. for 48 h, and confirmed by PCR using construct-specific primers.

The pDGB3omega1 modules harboring the ethylene-inducible reporters and the plant selectable marker were transformed into wild-type *Arabidopsis thaliana* ecotype Columbia (Col-0) as described (Alonso and Stepanova, 2015; Brumos, Zhao et al., 2019, Clough and Bent, 1998). Briefly, fresh *Agrobacterium* colonies were inoculated into 5 ml liquid LB supplemented with spectinomycin (100 µg mL$^{-1}$) (brandGold Biootechnology), rifampicin (20 µg mL$^{-1}$) (brandGold Biotechnology) and gentamycin (25 µg mL$^{-1}$) (brandGold Biotechnology) and grown overnight at 28° C. at 200 rpm. Next day, the 5 ml culture was split into two flasks containing 250 ml of liquid LB supplemented with spectinomycin (100 µg mL$^{-1}$) and grown overnight under the same conditions. Grown cultures were pulled together, pelleted by centrifugation and resuspended in 250 ml of dipping solution (5% glucose (Fisher) in water and 200 µl/L Silwet L-77 200 µl L$^{-1}$ (Lehle Seeds)). *Arabidopsis* Col-0 plants grown on soil under 16 h light/8 h dark cycle and 24° C. until inflorescences were 15 cm long were transformed by floral dipping as described (Clough and Bent, 1998) and recovered for 24-48 h under a plastic dome. Plants were then watered and cared for until maturity and their seeds were harvested in bulk. T1 transformants were selected in 20 µg ml$^{-1}$ phosphinothricin (GoldBio) in MS plates (4.33 g L$^{-1}$ Murashige & Skoog media (PhytoTech Labs), 10 g L$^{-1}$ sucrose (Fisher), 6 g L$^{-1}$ Bactroagar (Fisher)) supplemented with 300 µg ml-1 timentin (GoldBio) and propagated in soil (50:50 mix of SunGro propagation mix and Jolly Gardener pro-line growing mix) under same growing conditions. T3 plants homozygous for the modules were identified in phosphinothricin and confirmed by genotyping using construct-specific primers.

Seeds from T2 and T3 GUS-containing reporter lines, as well as T2, T3 and T4 fluorescent reporter lines, were surface-sterilized for 10-20 min with 50% (v/v) commercial bleach containing 3-4% sodium hypochlorite and 100 µl L$^{-1}$ Triton X-100 (Pharmacia). Bleach was removed by progressive washes with sterile di water and seeds were plated on plain MS (4.33 g L$^{-1}$ Murashige & Skoog media (PhytoTech Labs), 10 g L$^{-1}$ sucrose, 6 g L$^{-1}$ Bactoagar) or MS plates supplemented with 10 µM ACC (1-aminocyclopropane-1-carboxylic acid, PhytoTech Labs) or 200 ppm 1-MCP (1-methylcyclopropene, AgroFresh) using melted and pre-cooled sterile 0.7% (w/v) low-melting point agarose (Fisher). Plates with seeds were stratified at 4° C. for two days, exposed to light for 1-2 hours at room temperature to restart the clock, wrapped in aluminum foil and incubated for three days in the dark at 22° C. Plates for each treatment were kept separately from each other during the germination process to avoid the different treatments interfering with one another.

Three-day-old etiolated seedlings from the different treatments were fixed in cold 90% acetone and stained for GUS for 30 min, 2 h and overnight at 37° C. as described (Stepanova et al., 2005). Stained seedlings were optically cleared using freshly prepared ClearSee solution (Kurihara et al., 2015) for 7 days before imaging. Optically cleared GUS-stained seedlings were mounted on glass slides and imaged using a 5.0 RTV digital camera (Q Imaging, Surrey, BC, 904 Canada) under a Zeiss AxioSkop2 Plus microscope with Nomarski optics (Brumos, Zhao et al., 2019).

Three-day-old etiolated seedlings from T2, T3 and T4 fluorescent reporter lines germinated under different treatments (see above) were mounted on glass slides and imaged using a DFC365 FX camera and a Zeiss Axioplan microscope. Objective 5× was used to image full seedlings (100% intensity, 812.5 ms Exposure, 2.2 Gain) and objective 20× (17% intensity, 587.5 ms Exposure, 1.5 Gain) was utilized for imaging root tip, root sections, root-hypocotyl junctions, hypocotyl sections and apical hook regions in the seedlings.

Pre-selected seedlings from three-day-old etiolated T4 fluorescent reporter lines under epifluorescence microscopy, were analyzed at higher resolution using Zeiss LSM880 confocal microscope. The excitation/emission wavelengths for imaging were 488 nm/492-570 nm for YPet yellow fluorescent protein and the objective used was the water-immersion 40× (0.6 mm).

Phenotypic Analysis of Ethylene-Inducible Fluorescent Reporters

Figure 5:
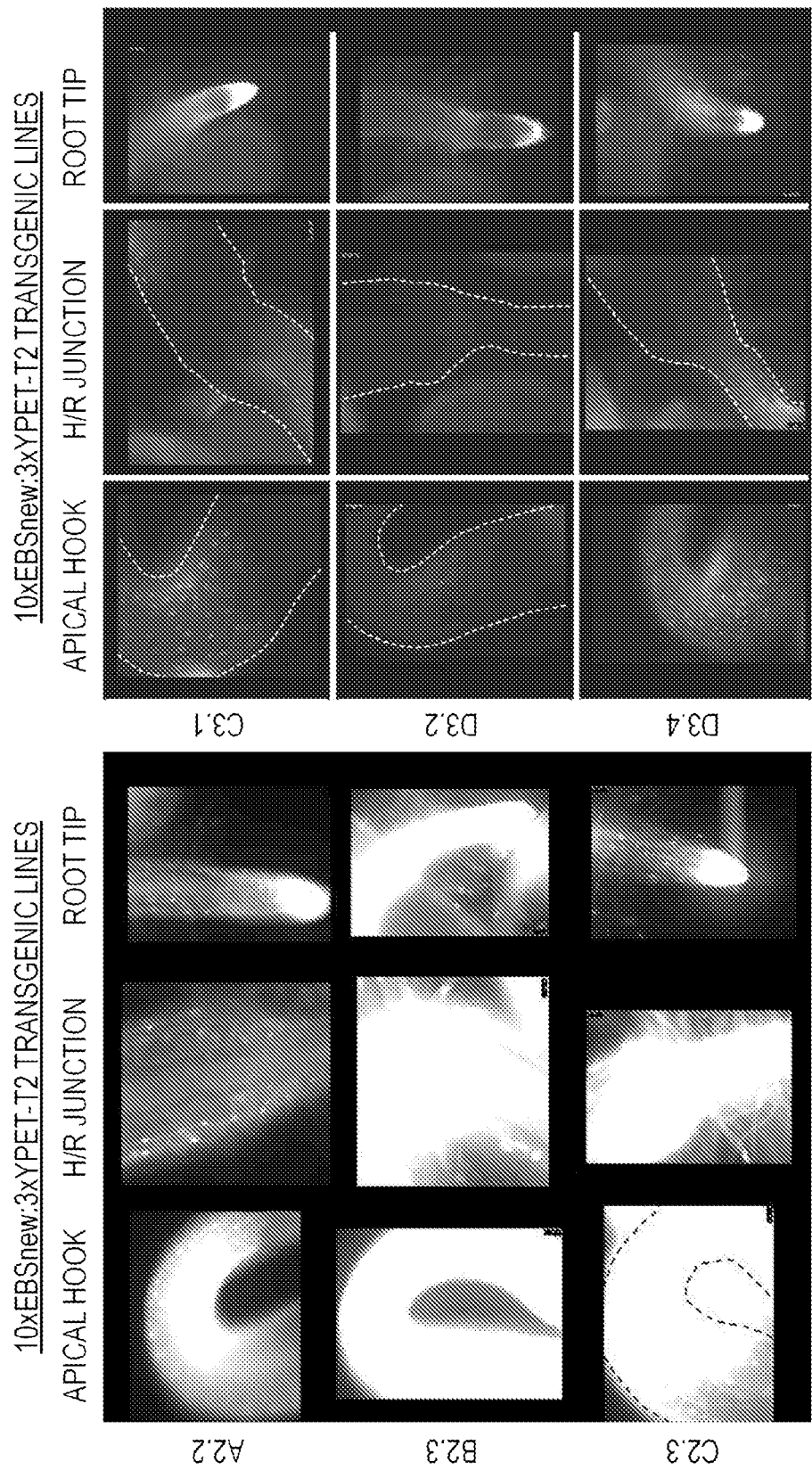
FIG. 5. Expression of 10xEBSnew:3xYPet and 10x:EBSclassic:3xYPet fluorescent reporters in T2 lines. While 10x:EBSclassic:3xYPet showed faint activity limited to apical hooks and root tips, 10xEBSnew:3xYPet displayed super-bright, saturating fluorescence that encompassed the entire plant. Images of three-day-old seedlings germinated in 10 µM ACC were captured at 20× magnification at the same fluorescence microscopy settings for all lines. Three independent transgenic T2 lines are shown for each reporter.
Figure 6:
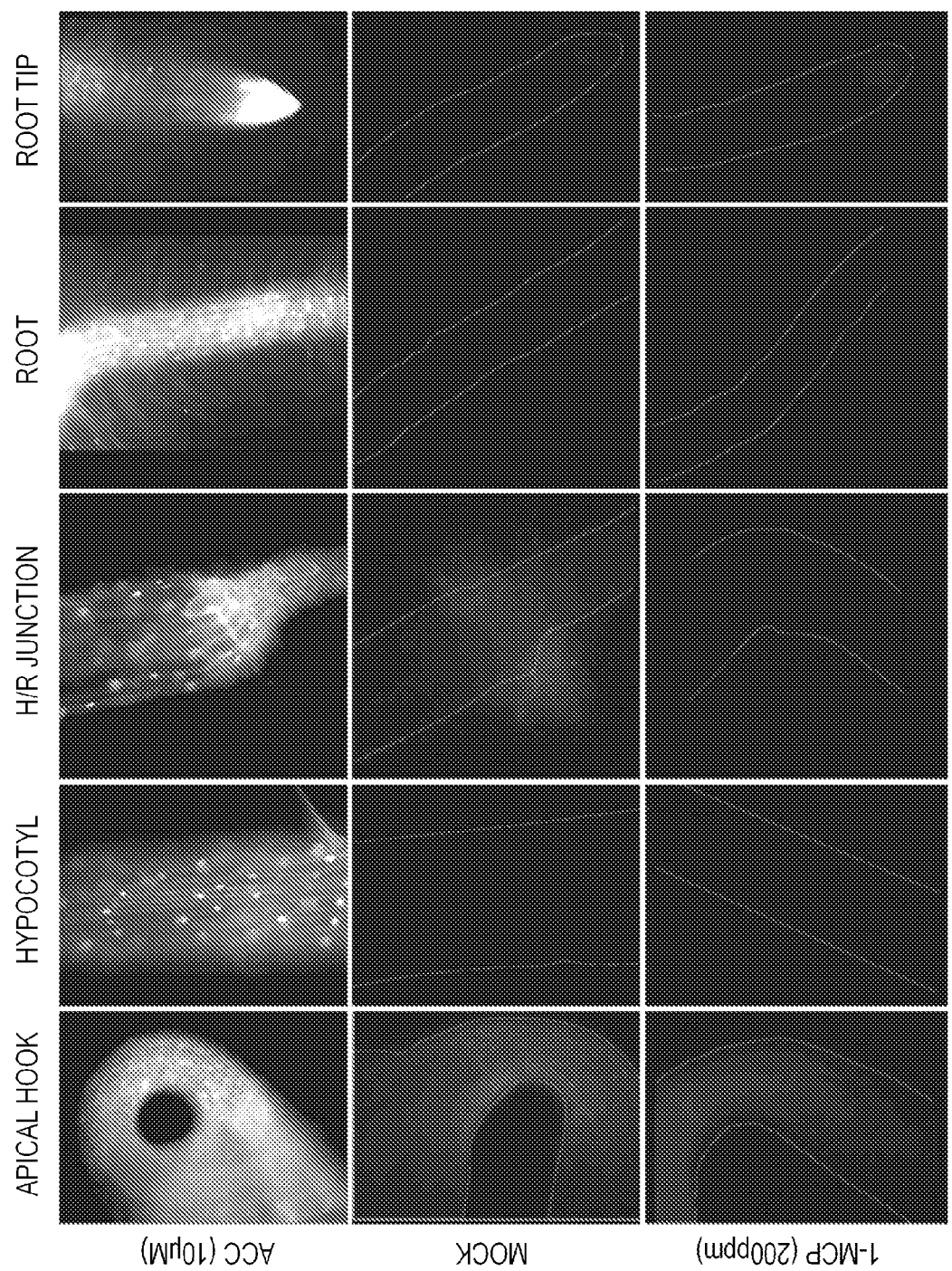
FIG. 6. The 10xEBSnew:3xYPet fluorescent reporter shows ethylene inducibility. The new reporter is highly active in the presence of 10 µM ACC, whereas the endogenous levels of ethylene (mock treatment) result in mild basal activity predominantly in the apical hook. No fluorescence is observed in the presence of 200 ppm 1-MCP. Images of three-day-old seedlings were captured with fluorescent microscopy at a 20× magnification from the transgenic T3 C2.3-2.3 line.

To test the functionality in planta of the new reporter constructs, 10xEBSnew, 10xEBSclassic and 2xEBS-S10 distal promoters fused to a triple yellow fluorescent protein (3xYPet) were individually transformed into *Arabidopsis thaliana* Col-0 wild type. Microscopy studies on three-day-old T2 seedlings germinated in the dark in the presence of the ethylene precursor ACC detected strong and moderate fluorescence for the 10xEBSnew:3xYPet and 10xEBSclassic:3xYPet reporters, respectively, in three independent lines examined per construct (FIG. 5). No fluorescence was seen for 2xEBS-S10:3xYPet transgenic lines (data not shown). In the presence of ACC, the expression of both 10xEBSnew: 3xYPet and 10xEBSclassic:3xYPet reporters was observed in root tips and apical hooks, but the fluorescence levels of the former were much stronger, reaching saturation in most tissues at the microscopy settings that detect only faint activity of the latter (FIG. 5). Unlike 10xEBSclassic:3xYPet, the 10xEBSnew: 3xYPet reporter was active in all parts of T2 seedlings, including cotyledons, apical hooks, hypocotyls, hypocotyl/root junctions and roots (FIG. 5 and FIG. 6).

Figure 7:
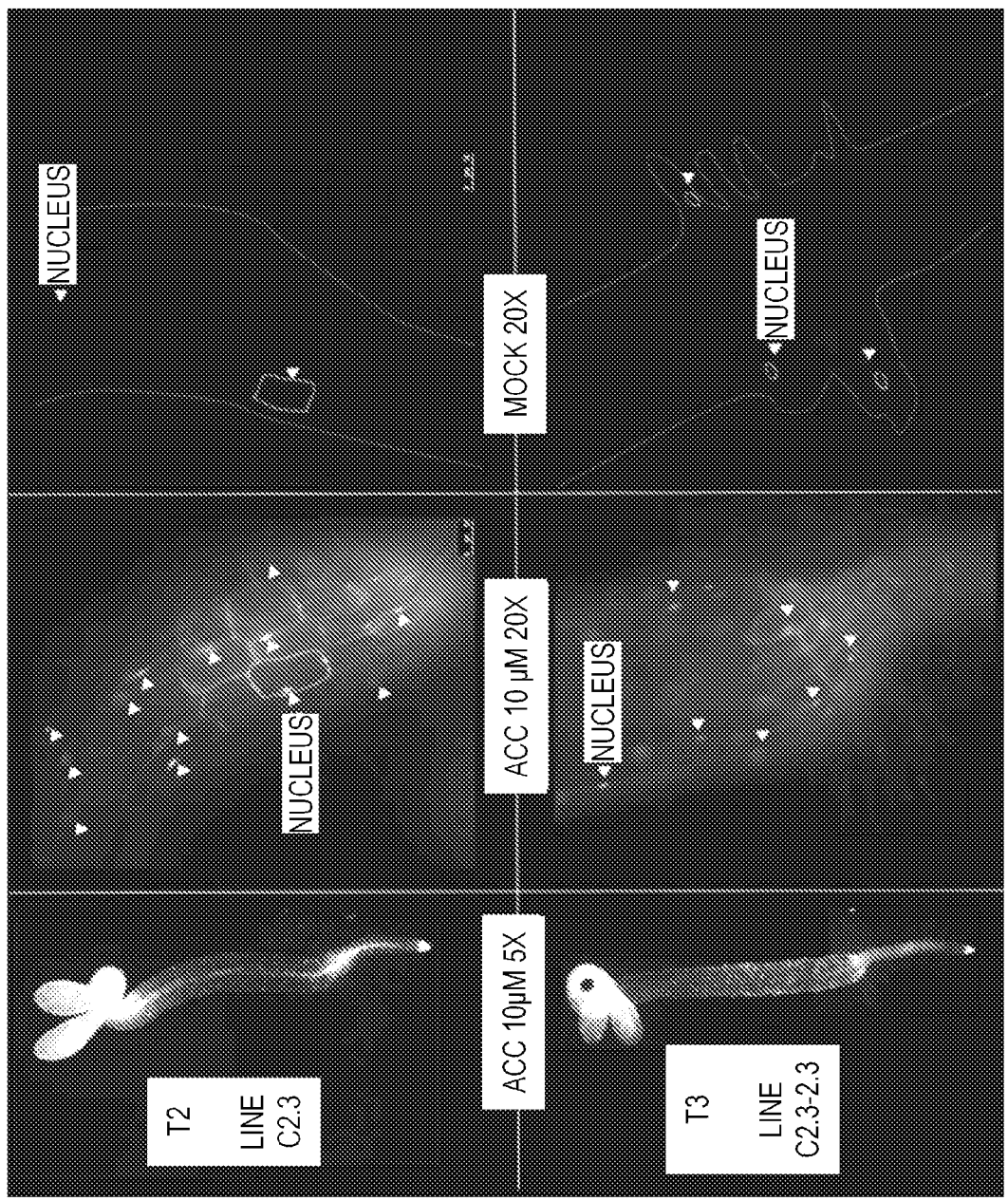
FIG. 7. The 10xEBSnew:3xYPet fluorescent reporter shows consistent expression pattern in T2 and T3 generations. The line C2.3 (T2 generation, heterozygous), and the daughter line C2.3-2.3 (T3 generation, homozygous) showed similar patterns and levels of expression in both mock and ACC treated samples. Images of three-day-old seedlings germinated with and without 10 µM ACC were captured by fluorescence microscopy at 5× and 20× magnification.

In order to test the inducibility and specificity of the 10xEBSnew distal promoter, the lines harboring the 10xEBSnew:3xYPet reporter where tested in: (1) control conditions (mock) to determine whether the reporter was able to detect endogenous levels of ethylene; (2) in the presence of the ethylene precursor (10 μM ACC) to demonstrate its ethylene-inducible behavior; and (3) in the presence of the ethylene receptor inhibitor (200 ppm 1-MCP) to establish the baseline of this reporter expression in the absence of endogenous ethylene signaling. The results shown in FIG. 6 indicate that 10xEBSnew:3xYPet was sensitive enough to detect endogenous level of ethylene, was strongly induced by ACC, and had no appreciable basal activity in the presence of 1-MCP. As expected, 10xEBSnew:3xYPet displayed predominantly nuclear fluorescence (FIG. 6 and FIG. 7) given that the construct harbored a nuclear localization signal. No silencing was observed in T2 and T3 generations (FIG. 6 and FIG. 7), supporting the notion of using non-perfect repeats of transcription factor binding sites as a way to minimize the likelihood of silencing triggered by otherwise repetitive synthetic promoters.

Figure 8:
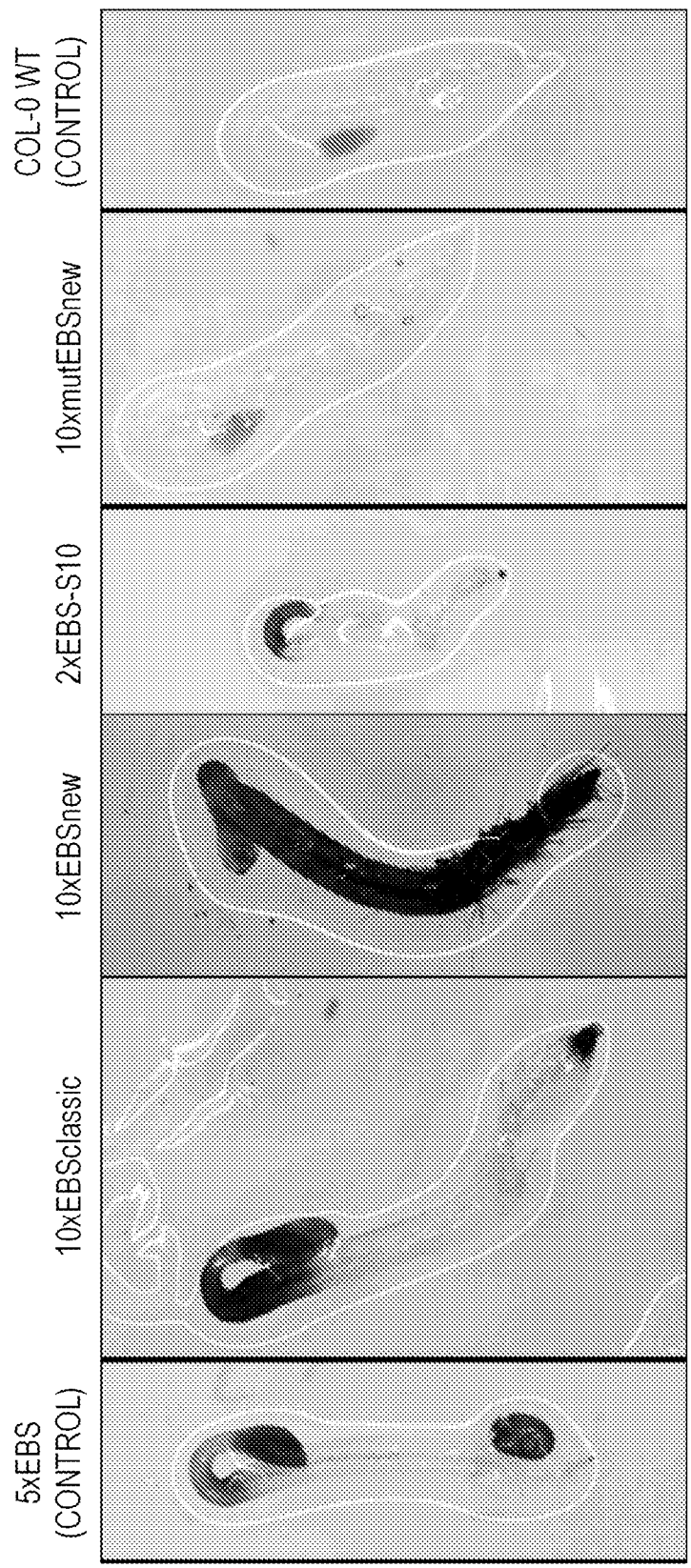
FIG. 8. GUS staining of five versions of ethylene reporters in ACC. Three-day-old T2 seedlings germinated in the dark in the presence of 10 µM ACC were stained for GUS overnight. The 10xEBSnew:GUS reporter showed maximum accumulation (saturated staining) throughout the plant. 10xEBSclassic:GUS was most active in the cotyledons, apical hooks and distal tips of the root and had a similar pattern of expression to that of homozygous 5xEBS:GUS, yet showed greater sensitivity in the root and lower hypocotyl. The 2xEBS-S10:GUS reporter presented a somewhat weaker activity largely restricted to the hook and root tip. The mut10xEBSnew:GUS reporter did not show any GUS activity and was indistinguishable from the non-transgenic Col-0 wild type. Note that the image of the 5xEBS:GUS positive control line (Stepanova et al, 2007) is the same as shown in FIG. 9 and is provided as a reference to enable cross-figure comparison.

Taken together, these results demonstrate that 10xEBSnew:3xYPet is a highly sensitive, ethylene-inducible fluorescent reporter suitable for the detection of both basal and ACC-triggered ethylene signaling and showing no appreciable background activity in the presence of 1-MCP.
Phenotypic Analysis of Ethylene-Inducible Histochemical Reporters To further increase the sensitivity of 10xEBSnew, the GUS (β-glucoronidase) version of the reporter was also built, along with its mutant variant, mut10xEBSnew (that harbors nucleotide substitutions in the core EIN3 target site, see Table 2), and previously mentioned 10xEBSclassic and 2xEBS-S10 reporter versions. Transgenic lines were generated in the *Arabidopsis thaliana* Col-0 wild type background and T2 lines were tested in three-day-old seedlings germinated in the dark in 10M ACC. Overnight GUS staining of transgenic seedlings showed that in the presence of ACC the 10xEBSnew:GUS reporter was highly active in all tissues (FIG. 8), consistent with the aforementioned results of the equivalent fluorescent reporter. In contrast, the activity of 10xEBSclassic:GUS, 5xEBS:GUS, and 2xEBS-S10:GUS was largely limited to specific organs (cotyledons, apical hooks and root tips) (FIG. 8). As expected, no GUS activity was observed in mut10xEBSnew:GUS lines, nor in the negative control Col-0 wild type plants (FIG. 8).

Figure 9:
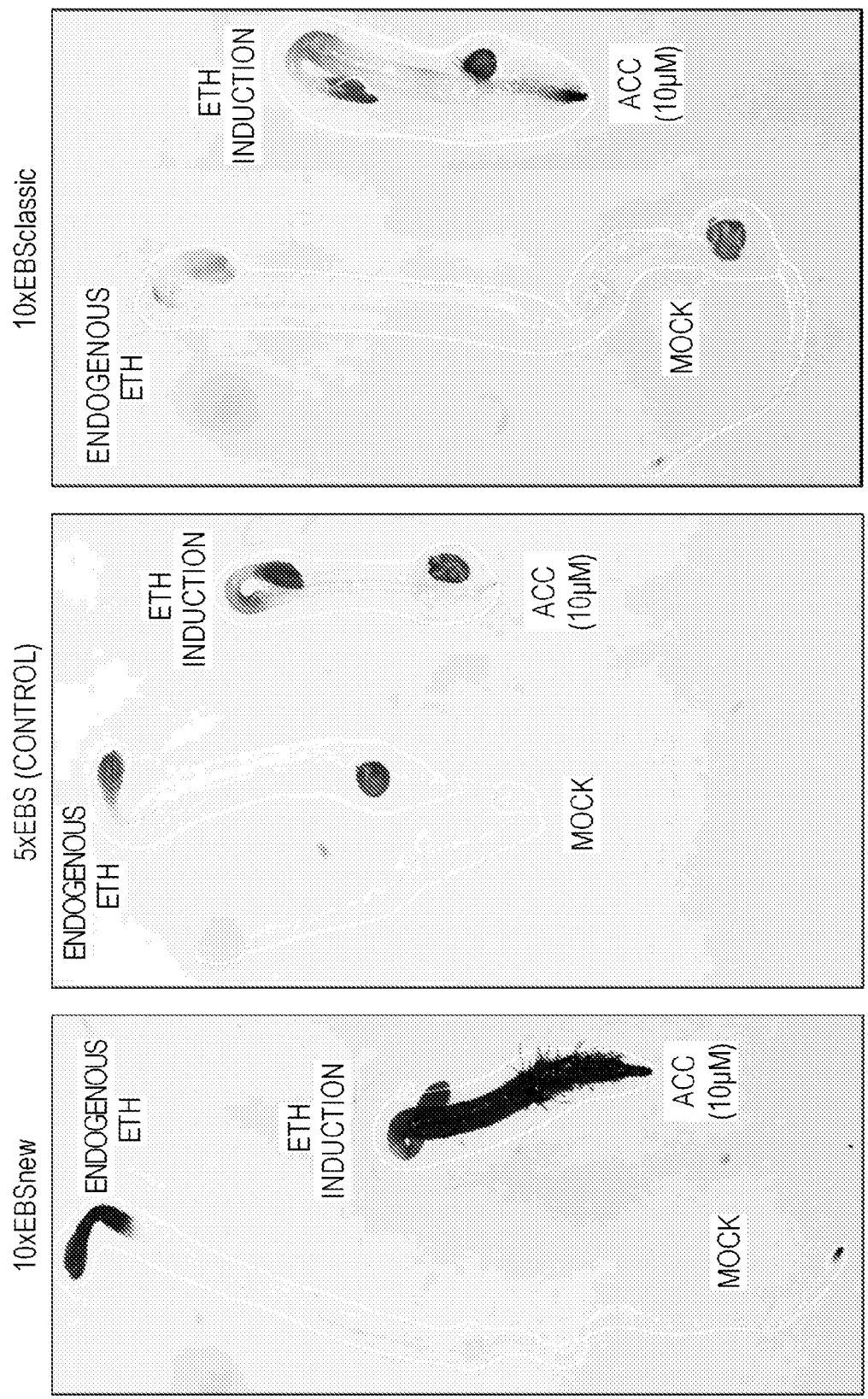
FIG. 9. Inducibility of the GUS ethylene reporters by ACC. Three-day-old seedlings harboring the 10xEBSnew:GUS, 10xEBSclassic:GUS and 5xEBS:GUS (image of the seedling in ACC shared within FIG. 8) reporters were germinated in control (mock) and 10 µM ACC-containing plates. Overnight staining confirmed the strongest ethylene-inducible expression of the 10xEBSnew:GUS reporter. Transgenic T2 lines were used in this experiment for both 10xEBSnew:GUS and 10xEBSclassic:GUS reporters. The image of the 5xEBS:GUS positive control line (Stepanova et al, 2007) in ACC is the same as shown in FIG. 8 and is provided as a reference to enable cross-figure comparison.

The inducibility of 10xEBSnew:GUS reporter was also examined in mock- and ACC-treated plants (FIG. 9). Consistent with the fluorescent line results, the 10xEBSnew promoter was able to detect endogenous levels of ethylene (having shown basal activity predominantly in the cotyledons, apical hooks and root tips) and was strongly inducible by ACC in the entire plant. Lower basal activity and limited induction by ACC was also seen for 10xEBSclassic:GUS and 5xEBS:GUS (FIG. 9). The 2xEBS-S10:GUS reporter did not show any staining in mock conditions, i.e. in the absence of exogenous treatment (data not shown), and displayed weak expression in the presence of ACC (FIG. 8).

Shorter staining of these transgenic lines revealed that the GUS activity of the 10xEBSnew:GUS reporter lines treated with ACC was detectable in apical hooks and roots within 10 minutes of incubation with the X-gluc substrate. In contrast, ACC-treated 10xEBSclassic:GUS did not present detectable reporter activity until after 1 hour of staining, and ACC-exposed 5xEBS:GUS and 2xEBS-S10 lines required several hours of staining to become detectable (data not shown).

These data demonstrate that 10xEBSnew outperforms all other constructs tested and represents a much more sensitive, strong, fast, and specific reporter suitable for monitoring both endogenous levels of ethylene activity and the response to a saturating exogenous ACC treatment in a large variety of tissues.

Example 3: Additional Ethylene Responsive Sequences

To generate the EBSnew construct (see Table 2 above), 21 bp-long natural DNA elements from the *Arabidopsis* genome were extracted from EIN3 ChIP-seq data. These sequences consist of an 11 bp-long natural 2EBS(-1) element flanked by 5 bp-long spacers naturally present in the genome upstream and downstream of the 11 bp core. The following two criteria were applied as filters to retrieve the best 2EBS(-1) elements: (1) the sequences are located within the EIN3 ChIP-seq peaks; and (2) those 2EBS(-1) sequences fall in the promoters of genes strongly inducible by ethylene.

The 21 bp-sequences from 18 top hits that passed these two criteria were randomly stacked together in groups of 10 to generate multiple versions of 10xEBS. The resulting tandems were then bioinformatically screened using position weight matrix for the presence of EIN3-unrelated transcription factor (TF) binding sites unintentionally generated at repeat junctions. The top ten 10xEBS sequence stacks (those with the lowest number and quality of undesired TF hits) obtained from multiple algorithm runs are listed below, with the individual wild-type (WT) repeat variants separated by a "|" and the core conserved 2EBS(-1) nucleotides in each repeat capitalized:

```
1 WT variant
                                                             (SEQ ID NO: 17)
gtatcATgCAaTGaATcatcc|tcttgGTtCAaTGaATcgagt|tcaatATaCAtTGtATtatgg|gattg ATtCAaTGcATtgttc|tctcaATtCAtTGcACtcgta|tttaaATaCAaTGcATcatta|gtccgATtCAtTGcA Caacaa|attggATaCAaTGtATtttgtc|aacagATaCAtTGaACattag|gagatATaCAtTGaATctata
```

-continued

2 WT variant (SEQ ID NO: 18)

gtatcATgCAaTGaATcatcc|tcttgGTtCAaTGaATcgagt|tctcaATtCAtTGcACtcgta|tttaaA

TaCAaTGcATcatta|gtccgATtCAtTGcACaacaa|attggATaCAaTGtATttgtc|aacagATaCAtTGa

ACattag|gattgATtCAaTGcATtgttc|tcaatATaCAtTGtATtatgg|gagatATaCAtTGaATctata

3 WT variant (SEQ ID NO: 19)

tctcgGTgCAaTGtATtggta|gtccgATtCAtTGcACaacaa|attggATaCAaTGtATttgtc|aacag

ATaCAtTGaACattag|gattgATtCAaTGcATtgttc|tcaatATaCAtTGtATtatgg|gtatcATgCAaTGa

ATcatcc|tcttgGTtCAaTGaATcgagt|tctcaATtCAtTGcACtcgta|gagatATaCAtTGaATctata

4 WT variant (SEQ ID NO: 20)

tctcgGTgCAaTGtATtggta|gtccgATtCAtTGcACaacaa|attggATaCAaTGtATttgtc|aacag

ATaCAtTGaACattag|gattgATtCAaTGcATtgttc|tcaatATaCAtTGtATtatgg|gtatcATgCAaTGa

ATcatcc|tcttgGTtCAaTGaATcgagt|tctcaATtCAtTGcACtcgta|gagatATaCAtTGaATctata

5 WT variant (SEQ ID NO: 21)

tctcgGTgCAaTGtATtggta|gtccgATtCAtTGcACaacaa|aacagATaCAtTGaACattag|gatt gATtCAaTGcATtgttc|tcaatATaCAtTGtATtatgg|gtatcATgCAaTGaATcatcc|tcttgGTtCAaTGa ATcgagt|tctcaATtCAtTGcACtcgta|tttaaATaCAaTGcATcatta|gagatATaCAtTGaATctata 6 WT variant (SEQ ID NO: 22)

tcaatATaCAtTGtATtatgg|gtatcATgCAaTGaATcatcc|tcttgGTtCAaTGaATcgagt|gtccg

ATtCAtTGcACaacaa|attggATaCAaTGtATttgtc|aacagATaCAtTGaACattag|gattgATtCAaTG cATtgttc|tctcaATtCAtTGcACtcgta|tttaaATaCAaTGcATcatta|gagatATaCAtTGaATctata 7 WT variant (SEQ ID NO: 23)

tctcgGTgCAaTGtATtggta|gattgATtCAaTGcATtgttc|tcaatATaCAtTGtATtatgg|gtatcA

TgCAaTGaATcatcc|tcttgGTtCAaTGaATcgagt|tctcaATtCAtTGcACtcgta|gtccgATtCAtTGcA

Caacaa|attggATaCAaTGtATttgtc|aacagATaCAtTGaACattag|gagatATaCAtTGaATctata

8 WT variant (SEQ ID NO: 24)

tcaatATaCAtTGtATtatgg|gtatcATgCAaTGaATcatcc|tcttgGTtCAaTGaATcgagt|tctca

ATtCAtTGcACtcgta|tttaaATaCAaTGcATcatta|gattgATtCAaTGcATtgttc|gtccgATtCAtTGcA

Caacaa|attggATaCAaTGtATttgtc|aacagATaCAtTGaACattag|gagatATaCAtTGaATctata

9 WT variant (SEQ ID NO: 25)

tcaagATtCAaTGaACtccgt|tctcaATtCAtTGcACtcgta|tttaaATaCAaTGcATcatta|gattgA

TtCAaTGcATtgttc|tcaatATaCAtTGtATtatgg|gtatcATgCAaTGaATcatcc|tcttgGTtCAaTGaAT cgagt|gtccgATtCAtTGcACaacaa|aacagATaCAtTGaACattag|gagatATaCAtTGaATctata 10 WT variant (SEQ ID NO: 26)

tctcgGTgCAaTGtATtggta|gtccgATtCAtTGcACaacaa|aacagATaCAtTGaACattag|gatt gATtCAaTGcATtgttc|tctcaATtCAtTGcACtcgta|gaaagATaCAtTGaATgcgag|gtatcATgCAaT GaATcatcc|tcttgGTtCAaTGaATcgagt|tcaatATaCAtTGtATtatgg|gagatATaCAtTGaATctata Of these ten 10xEBS stacks, we chose the first sequence, WT variant 1 (SEQ ID NO:17), for further analysis. To optimize this sequence, the potential transcription factor binding sites at the flanks of each repeat were eliminated by replacing the key nucleotides within those target sites, thus likely abolishing the binding of undesired TFs. The resulting improved version of the 10xEBS variant 1 was named EBSnew.

```
EBSnew (with the replaced, non-natural flanking
nucleotides capitalized)
                                        (SEQ ID NO: 14)
gtatcatgcaatgaatcaAcc|tcttggttcaatgaatcgagt|Gcaata tacattgtattatgg|gatGgattcaatgcatCgttc|tctcaattcatt gcactcTta|tttaaatacaatgcatcaGta|gtccgattcattgcacaa cGa|attggatacaatgtatttgtG|aacagatacattgaacattag|ga gaGatacattgaatctata
```

EBSnew is a tandem of 10 semi-synthetic, buffered 2EBS (−1) elements spaced in a manner that places EIN3 dimers on the same side of the DNA double helix, with each 21 bp imperfect repeat taking exactly two helical turns.

A mutant version of this sequence, mutEBSnew, in which the core conserved 2EBS(−1) nucleotides presumed necessary for EIN3 binding were mutated (with one conserved nucleotide replaced per each half-site), was also generated to be employed as a negative control.

```
mutEBSnew (with the
mutated core nucleotides bolded) (SEQ ID NO: 15):
gtatcaggcaatgactcaAcc|tcttggttgaacgaatcgagt|Gcaatat agattgtaatatgg|gatGgattaaacgcatCgttc|tctcaattcgtagc actcTta|tttaaatactaggcatcaGta|gtccgattccttgctcaacGa

|attggctacaatgtaattgtG|aacagatagatagaacattag|gagaGc tacattgaaactata
```

Both the optimized sequence, EBSnew, and its mutant version, mutEBSnew, were commercially synthesized and cloned into the GoldenBraid 3.0 entry vector, pUPD2, confirmed by sequencing, and used in the generation of reporter constructs.

Twenty products of two additional runs, A and B, of the algorithm that optimized the sequences of ten best 10xEBS sequence stacks by eliminating the undesired TF-binding sites at the junctions of stacked WT variants 1 though 10 are listed below. These improved sequences should be functionally equivalent to the characterized EBSnew sequence, but have not been experimentally validated.

Additional EBSnew variants 1 through 10 generated in A & B runs of the algorithm (with the replaced, non-natural flanking nucleotides capitalized) are provided below.

```
1a-10a
                                                      (SEQ ID NO: 27)
gtatcatgcaatgaatcatcctcCtggttcaatgaatcgagttcaaAatacattgtattatgggGttgattcaatgcattgttc GctcaattcattgcactcTtatttaaatacaatgcatcCttagtccgattcattgcacaacGaattggatacaatgtatttgtAaacagat acattgaacattaTgagatatacattgaatctata (SEQ ID NO: 28)
gtatcatgcaatgaatcatcctcCtggttcaatgaatcgagCtctcaattcattgcactcTtatttaaatacaatgcatcCttag tccgattcattgcacaacGaattggatacaatgtatttgtAaacagatacattgaacaGtaggattgattcaatgcattgtGctcaatata cattgtattatgggagaAatacattgaatctata (SEQ ID NO: 29)
tctcggtgcaatgtattggtagCccgattcattgcacaacGaattggatacaatgtatttgtAaacagatacattgaacattT ggattgattcaatgcattgttctcTatatacattgtattatgggtatTatgcaatgaatcaAcctcttggttcaatgaatcgagtGctcaatt cattgcactcAtagagatatacattgaatctata (SEQ ID NO: 30)
tctcggtgcaatgtattggtagCccgattcattgcacaacGaattggatacaatgtatttgtAaacagatacattgaacatta gTattgattcaatgcattgttctcTatatacattgtattatgggtatTatgcaatgaatcatcTtcttggttcaatgaatcgagtGctcaatt cattgcactcAtagagatatacattgaatctata (SEQ ID NO: 31)
tctcggtgcaatgtattggtagCccgattcattgcacaaTaaaacagatacattgaacaAtaggattgattcaatgcattgtt ctcTatatacattgtattatgggtatTatgcaatgaatcatcctcCtggttcaatgaatcgagtGctcaattcattgcactcTtatttaaata caatgcatcaGtagagatatacattgaatctata (SEQ ID NO: 32)
tcaatatacattgtattatgggtatAatgcaatgaatcatcTtcttggttcaatgaatcgGtgtccgattcattgcacaacGa attggatacaatgtatttgtGaacagatacattgaacattagTattgattcaatgcattgttctctcTattcattgcactcgtTtttaaataca atgcatcaGtagagatatacattgaatctata
```

(SEQ ID NO: 33)
tctcggtgcaatgtattCgtagattgattcaatgcattgttctcTatatacattgtattatgggtatTatgcaatgaatcatcctc
CtggttcaatgaatcgagttctcTattcattgcactcgtagtccAattcattgcacaacGaattggatacaatgtatttgtAaacagatac
attgaacattaggagaGatacattgaatctata (SEQ ID NO: 34)
tcaatatacattgtattatgggtatAatgcaatgaatcaCcctcttggttcaatgaatcgagttctcCattcattgcactcCtatt
taaatacaatgcatcCttagattgattcaatgcattgttcTtccgattcattgcacaacGaattggatacaatgtatttgtGaacagataca
ttgaacattaggagaGatacattgaatctata (SEQ ID NO: 35)
tcaagattcaatgaactccTttctcaattcattgcactAgtatttaaatacaatgcatcaGtagattgattcaatgcattgttctc
TatatacattgtattatgggtatTatgcaatgaatcaAcctcttggttcaatgaatcgagtgtccAattcattgcacaaTaaaacagata
cattgaacattaTgagatatacattgaatctata (SEQ ID NO: 36)
tctcggtgcaatgtattggtagCccgattcattgcacaaTaaaacagatacattgaacattTggattgattcaatgcattgttc
tctGaattcattgcactcgtagCaagatacattgaatgcgaggtatAatgcaatgaatcatcctcttTgttcaatgaatcgagCtcaata
tacattgtattatgggagaAatacattgaatctata 1b-10b (SEQ ID NO: 37)
gtatcatgcaatgaatcaAcctcttggttcaatgaatcgagttcaTtatacattgtattatgggatGgattcaatgcatAgttct
ctcaattcattgcactcTtatttaaatacaatgcatcCttagtccgattcattgcacaacGaattggatacaatgtatttgtGaacagatac
attgaacaAtaggagatatacattgaatctata (SEQ ID NO: 38)
gtatcatgcaatgaatcaAcctcttggttcaatgaatcgagtGctcaattcattgcactcTtatttaaatacaatgcatcCtta
gtccgattcattgcacaacGaattggatacaatgtatttgtAaacagatacattgaacattagTattgattcaatgcattgtGctcaatata
cattgtattatgAgagatatacattgaatctata (SEQ ID NO: 39)
tcaagattcaatgaactccTttctcaattcattgcactcTtagattgattcaatgcattgttctcTatatacattgtattatgggtat
TatgcaatgaatcatcctcCtggttcaatgaatcgagtgtccAattcattgcacaacGaattggatacaatgtatttgtAaacagatac
attgaacatAaggagatatacattgaatctata (SEQ ID NO: 40)
tctcggtgcaatgtattggtagtGcgattcattgcacaacGaattggatacaatgtatttgtAaacagatacattgaacaGta
ggattgattcaatgcattgttctcTatatacattgtattatgggtatTatgcaatgaatcatcctcCtggttcaatgaatcgagtGctcaatt
cattgcactcAtagagatatacattgaatctata (SEQ ID NO: 41)
tctcggtgcaatgtattggAagtccgattcattgcacaaTaaaacagatacattgaacattaggaCtgattcaatgcattgtt
ctcTatatacattgtattatgggtatTatgcaatgaatcaAcctcttggttcaatgaatcgagtGctcaattcattgcactcTtatttaaata
caatgcatcaAtagagatatacattgaatctata (SEQ ID NO: 42)
tcaatatacattgtattatgggtatAatgcaatgaatcatcctAttggttcaatgaatcgagtgtTcgattcattgcacaacGa
attggatacaatgtatttgtGaacagatacattgaacattagAattgattcaatgcattgttctcAcaattcattgcactcCtatttaaatac
aatgcatcaCtagagatatacattgaatctata (SEQ ID NO: 43)
tctcggtgcaatgtattggtagCttgattcaatgcattgttctcTatatacattgtattatgggtatTatgcaatgaatcaCcctc
ttggttcaatgaatcgagttctTaattcattgcactAgtagtccgattcattgcacaacGaattggatacaatgtatttgtGaacagatac
attgaacattaTgagatatacattgaatctata (SEQ ID NO: 44)
tcaatatacattgtattatgggtatAatgcaatgaatcatGctcttggttcaatgaatcgagttctTaattcattgcactcgtTttt aaatacaatgcatcaCtagattgattcaatgcatAgttcgtccgattcattgcacaacGaattggatacaatgtatttgtAaacagatac attgaacaGtaggagatatacattgaatctata (SEQ ID NO: 45)
tcaagattcaatgaactccTtctcaattcattgcactcgtTtttaaatacaatgcatcaGtagattgattcaatgcattgttctc TatatacattgtattatgggtatTatgcaatgaatcCtcctcttggttcaatgaatcgagtgtTcgattcattgcacaaTaaaacagatac attgaacattaggagaGatacattgaatctata (SEQ ID NO: 46)
tctcggtgcaatgtattggAagtccgattcattgcacaaTaaaacagatacattgaacatCaggattgattcaatgcattgtt ctctcTattcattgcactcgtagTaagatacattgaatgcgaggtatAatgcaatgaatcatcctAttggttcaatgaatcgagtGcaat atacattgtattatgggCgatatacattgaatctata

Example 4: The EBSnew Promoter Enables Ethylene Signal Detection in Tomato Plants The EBSnew distal promoter (see Example 2) was combined with a minimal (−46) 35S promoter, the mCherry red fluorescent protein coding sequence, the peroxisome targeting sequence KSRM, and the 35S terminator using the Golden Braid technology as previously described in Example 2. The final constructs were transformed into *Agrobacterium tumefaciens* and used to generate transgenic tomato (*Solanum lycopersicum* cv. M82) using the standard callus transformation protocol as described in Patel et al. (2015, Tomato plants overexpressing a celery mannitol dehydrogenase (MTD) have decreased susceptibility to *Botrytis cinerea*. American Journal of Plant Sciences, 6, 1116-1125).

To examine the effects of ethylene on the expression of the mCherry reporter, seeds of T1 tomato plants (*Solanum lycopersicum* cv. M82) were surface-sterilized in 70% (v/v) ethanol for 3 minutes, followed by 30% (v/v) commercial bleach (1.8% sodium hypochlorite final concentration) for 7 minutes, and rinsed five times with sterile deionized water to wash the bleach off. Sterilized seeds were placed in Magenta™ boxes containing solid (5 g/L agar) medium with half-strength Murashige & Skoog basal salts, 1% sucrose pH 6, and grown for four days in the dark. Wild type M82 and transgenic tomato seedlings harboring the 10xEBSnew:mCherry reporter were then transferred to fresh Petri dishes containing the media described above supplemented or not supplemented with the ethylene precursor 1-aminocyclopropane-1-carboxylic acid (ACC, 10 µM), kept for 24 hours in the dark at room temperature and imaged with the fluorescence microscope (Zeiss Axioimager M.2).

Figure 10:
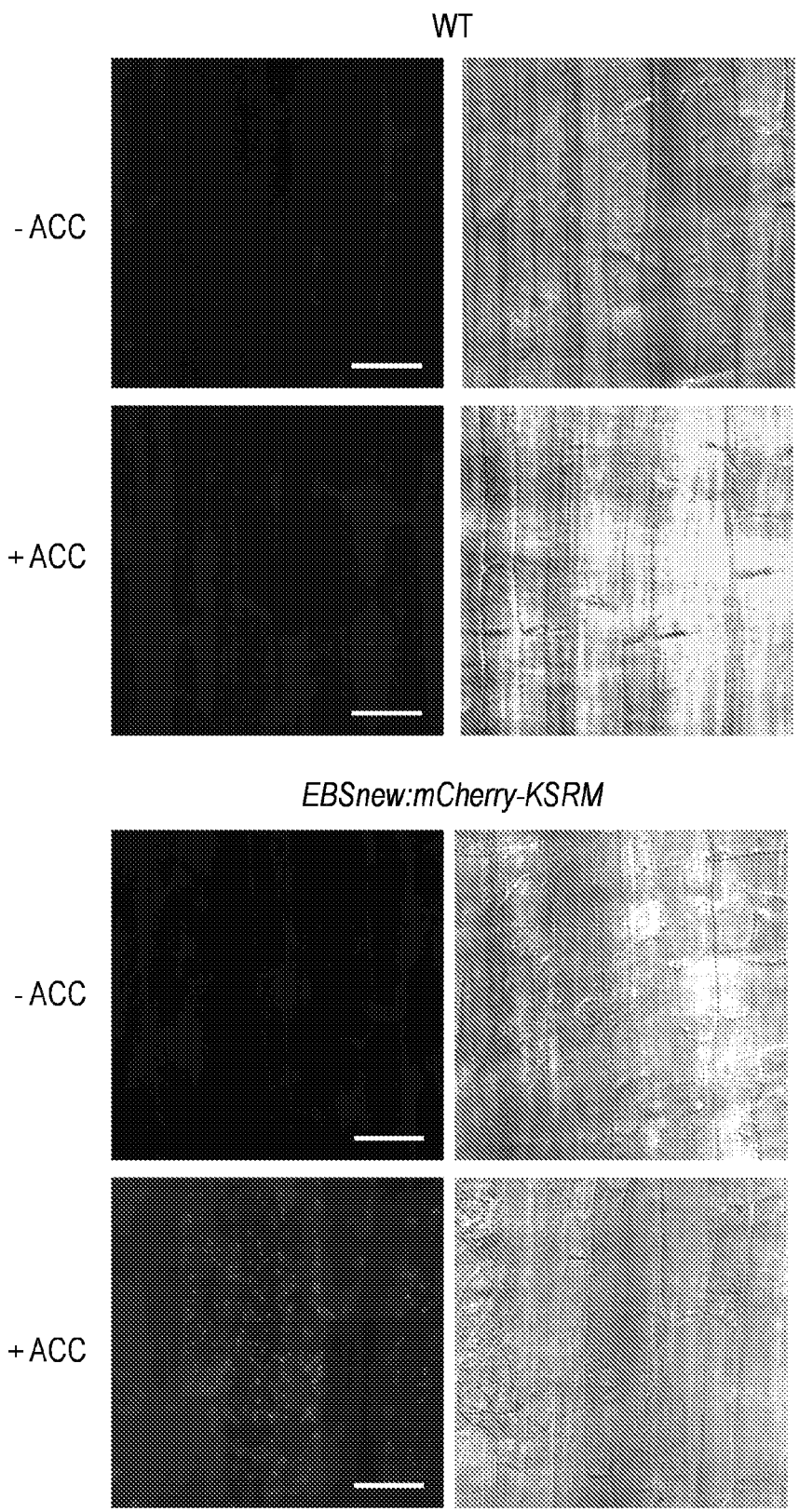
FIG. 10. The 10xEBSnew:mCherry reporter shows ethylene inducibility in tomato plants. The new ethylene reporter is highly active in tomato plants treated with 10 µM ethylene precursor ACC for 24 hours. Only background levels of fluorescence are detected in transgenic tomato plants harboring the reporter construct but not treated with ACC or in wild-type plants not carrying the transgenic construct. Images of 5-day-old T1 tomato seedlings were captured with a Zeiss Axioimager M.2 fluorescent microscope at 40× magnification. The mCherry protein was targeted to the peroxisomes using the KSRM tag fused at the carboxy-terminus of the mCherry reporter. Scale bar=25 μm.

Under the fluorescence microscope (Zeiss Axioimager M.2), no mCherry fluorescence signal in the peroxisomes was observed in wild type roots or in transgenic roots not exposed to the ethylene precursor ACC (FIG. 10). On the other hand, transgenic roots treated overnight with 10 µM ACC showed a clear expression of mCherry in the peroxisomes.

These results indicate that the EBSnew promoter sequences can be used to generate highly sensitive, ethylene-inducible reporters using different fluorescent proteins and subcellular localization signals not only in *Arabidopsis* but also in very distantly related plant species such as tomato and potentially many other plant species.

The foregoing is illustrative of the present invention, and is not to be construed as limiting thereof. The invention is defined by the following claims, with equivalents of the claims to be included therein.

That which is claimed is:

1. A recombinant nucleic acid construct comprising two or more directly adjoining ethylene binding sequences (EBS), wherein each of the EBS is a sequence of Formula I (SEQ ID NO:48):

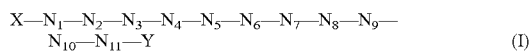

wherein:
$N_1$ is A or G;
$N_2$ is T;
$N_3$ is G, T or A;
$N_4$ is C;
$N_5$ is A;
$N_6$ is A or T;
$N_7$ is T;
$N_8$ is G;
$N_9$ is A, T or C;
$N_{10}$ is A;
$N_{11}$ is T or C; and
X and Y are each independently present or absent and when present is each independently a spacer sequence comprising 1 to 50 nucleotides.

2. The recombinant nucleic acid construct of claim 1, wherein the two or more EBS of Formula I comprise two or more of SEQ ID NOS:1-11.

3. The recombinant nucleic acid construct of claim 1, wherein the two or more EBS of Formula I are operably linked to a core promoter, optionally wherein the core promoter is within 0 to 2,000 base pairs downstream (3') of the two or more EBS of Formula I.

4. The recombinant nucleic acid construct of claim 1, wherein the two or more EBS of Formula I comprise EBS which are not identical with one another.

5. The recombinant nucleic acid construct of claim 1, wherein the two or more EBS of Formula I comprise four or five EBS of Formula I.

6. The recombinant nucleic acid construct of claim 1, wherein the two or more EBS of Formula I comprise six, seven, eight, or nine EBS of Formula I.

7. The recombinant nucleic acid construct of claim 1, wherein the two or more EBS of Formula I comprise ten, eleven or twelve EBS of Formula I, and optionally up to 50, 75 or 100 EBS of Formula I.

8. The recombinant nucleic acid construct of claim 1, wherein the EBS of Formula I does not comprise a transcription factor binding element that is not an EBS of Formula I.

9. The recombinant nucleic acid construct of claim 8, wherein the construct comprises a sequence selected from the group consisting of SEQ ID NOS:14 and 27-46; and sequences with 90, 91, 92, 93, 94, 95, 96, 97, 98, or 99% identity thereto.

10. An expression cassette comprising the recombinant nucleic acid construct of claim 1 operably linked to a core promoter, and optionally one or more of a subcellular localization signal, a nucleic acid of interest, and a transcriptional terminator.

11. The expression cassette of claim 10, wherein the nucleic acid of interest is present and encodes a reporter protein.

12. The expression cassette of claim 10, wherein the nucleic acid of interest is present and encodes an antioxidant protein, a toxin, a vitamin-biosynthesis protein, a pigment protein, a pathogen defense protein, or a flavor inducing enzyme.

13. The expression cassette of claim 10, wherein the expression cassette comprises, from 5' to 3', the recombinant nucleic acid construct, the minimal promoter, the nucleic acid of interest, and the transcriptional terminator.

14. A plant cell comprising the expression cassette of claim 10.

15. A plant comprising the plant cell of claim 14.

16. The plant of claim 15, wherein the plant is *Arabidopsis*, tomato, tobacco, maize, or rice.

17. A method of modulating the expression of a nucleic acid of interest in a plant in response to ethylene, the method comprising
    introducing into a plant cell the expression cassette of claim 10 to produce a transformed plant cell;
    regenerating a transformed plant from the transformed plant cell; and
    exposing the transformed plant, or a plant part or plant cell therefrom, to the ethylene, whereby the nucleic acid of interest is expressed.

18. The method of claim 17, wherein the recombinant nucleic acid construct and the nucleic acid of interest are integrated into the genome of the plant.

19. The method of claim 17, wherein the recombinant nucleic acid construct and the nucleic acid of interest are not integrated into the genome of the plant.

20. The method of claim 17, wherein the exposing is carried out by applying ethylene or an ethylene precursor to the transformed plant, or plant part or plant cell therefrom.

* * * * *

UNITED STATES PATENT AND TRADEMARK OFFICE
CERTIFICATE OF CORRECTION

Page 1 of 1

PATENT NO. : 12,319,919 B2
APPLICATION NO. : 18/002134
DATED : June 3, 2025
INVENTOR(S) : Stepanova et al.

It is certified that error appears in the above-identified patent and that said Letters Patent is hereby corrected as shown below:

In the Specification

Column 1, Line 25: Please correct "5051-983 ST25.txt," to read --5051-983_ST25.txt,--

Column 10, Line 48: Please correct "anon-limiting" to read --a non-limiting--

Column 23, Line 47: Please correct "10M" to read --10μM--

Column 31, Line 42: Please correct "off" to read --off.--

Signed and Sealed this
Twenty-third Day of September, 2025

John A. Squires
*Director of the United States Patent and Trademark Office*

SEQUENCE LISTING

```
<160> NUMBER OF SEQ ID NOS: 51

<210> SEQ ID NO 1
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t, each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 1
nnnnnnnnnn nnnnnnnnnn nnnnnnnnnn nnnnnnnnnn nnnnnnnnnn atgcaatgaa     60
```
tnnnnnnnnn nnnnnnnnnn nnnnnnnnnn nnnnnnnnnn nnnnnnnnnn n    111

<210> SEQ ID NO 2
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 2
nnnnnnnnnn nnnnnnnnnn nnnnnnnnnn nnnnnnnnnn nnnnnnnnnn gttcaatgaa    60
tnnnnnnnnn nnnnnnnnnn nnnnnnnnnn nnnnnnnnnn nnnnnnnnnn n    111

<210> SEQ ID NO 3
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 3
nnnnnnnnnn nnnnnnnnnn nnnnnnnnnn nnnnnnnnnn nnnnnnnnnn gtgcaatgta    60
tnnnnnnnnn nnnnnnnnnn nnnnnnnnnn nnnnnnnnnn nnnnnnnnnn n    111

<210> SEQ ID NO 4
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 4
nnnnnnnnnn nnnnnnnnnn nnnnnnnnnn nnnnnnnnnn nnnnnnnnnn atacattgaa    60
cnnnnnnnnn nnnnnnnnnn nnnnnnnnnn nnnnnnnnnn nnnnnnnnnn n    111

<210> SEQ ID NO 5
<211> LENGTH: 111
<212> TYPE: DNA

```
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 5
nnnnnnnnnn nnnnnnnnnn nnnnnnnnnn nnnnnnnnnn nnnnnnnnnn atacattgaa      60
tnnnnnnnnn nnnnnnnnnn nnnnnnnnnn nnnnnnnnnn nnnnnnnnnn n              111

<210> SEQ ID NO 6
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 1-50 is either absent or present

<400> SEQUENCE: 6
nnnnnnnnnn nnnnnnnnnn nnnnnnnnnn nnnnnnnnnn nnnnnnnnnn atacattgta      60
tnnnnnnnnn nnnnnnnnnn nnnnnnnnnn nnnnnnnnnn nnnnnnnnnn n              111

<210> SEQ ID NO 7
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 7
nnnnnnnnnn nnnnnnnnnn nnnnnnnnnn nnnnnnnnnn nnnnnnnnnn atacaatgca      60
tnnnnnnnnn nnnnnnnnnn nnnnnnnnnn nnnnnnnnnn nnnnnnnnnn n              111

<210> SEQ ID NO 8
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
```

```
            positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 8
nnnnnnnnnn nnnnnnnnnn nnnnnnnnnn nnnnnnnnnn nnnnnnnnnn atacaatgta      60
tnnnnnnnnn nnnnnnnnnn nnnnnnnnnn nnnnnnnnnn nnnnnnnnnn n              111

<210> SEQ ID NO 9
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 9
nnnnnnnnnn nnnnnnnnnn nnnnnnnnnn nnnnnnnnnn nnnnnnnnnn attcaatgca      60
tnnnnnnnnn nnnnnnnnnn nnnnnnnnnn nnnnnnnnnn nnnnnnnnnn n              111

<210> SEQ ID NO 10
<211> LENGTH: 111
<212> TYPE: DNA
<213> ORGANISM: Artificial Sequence
<220> FEATURE:
<223> OTHER INFORMATION: Formula I Example seqeunce
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 10
nnnnnnnnnn nnnnnnnnnn nnnnnnnnnn nnnnnnnnnn nnnnnnnnnn attcaatgaa      60
cnnnnnnnnn nnnnnnnnnn nnnnnnnnnn nnnnnnnnnn nnnnnnnnnn n              111

<210> SEQ ID NO 11
<211> LENGTH: 111
<212> TYPE: DNA
<213> ORGANISM: Artificial Sequence
<220> FEATURE:
<223> OTHER INFORMATION: Formula I Example Sequence
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 1-50 is either absent or present
```

<400> SEQUENCE: 11
nnnnnnnnnn nnnnnnnnnn nnnnnnnnnn nnnnnnnnnn nnnnnnnnnn attcattgca    60
cnnnnnnnnn nnnnnnnnnn nnnnnnnnnn nnnnnnnnnn nnnnnnnnnn n            111

<210> SEQ ID NO 12
<211> LENGTH: 400
<212> TYPE: DNA
<213> ORGANISM: Artificial Sequence
<220> FEATURE:
<223> OTHER INFORMATION: EBS classic x10 promoter

<400> SEQUENCE: 12
agcctcatga tcaaaggggg gatgcactat ttaaggatct agcctcatga tcaaaggggg    60
gatgcactat ttaaggatct agcctcatga tcaaaggggg gatgcactat ttaaggatct   120
agcctcatga tcaaaggggg gatgcactat ttaaggatct agcctcatga tcaaaggggg   180
gatgcactat ttaaggatct agcctcatga tcaaaggggg gatgcactat ttaaggatct   240
agcctcatga tcaaaggggg gatgcactat ttaaggatct agcctcatga tcaaaggggg   300
gatgcactat ttaaggatct agcctcatga tcaaaggggg gatgcactat ttaaggatct   360
agcctcatga tcaaaggggg gatgcactat ttaaggatct                        400

<210> SEQ ID NO 13
<211> LENGTH: 280
<212> TYPE: DNA
<213> ORGANISM: Artificial Sequence
<220> FEATURE:
<223> OTHER INFORMATION: 2 EBS-S10 x10 promoter

<400> SEQUENCE: 13
aagatacatg caaaaaagca tgtatcttaa gatacatgca aaaagcatg tatcttaaga    60 tacatgcaaa aaagcatgta tcttaagata catgcaaaaa agcatgtatc ttaagataca   120
tgcaaaaaag catgtatctt aagatacatg caaaaaagca tgtatcttaa gatacatgca   180
aaaaagcatg tatcttaaga tacatgcaaa aaagcatgta tcttaagata catgcaaaaa   240
agcatgtatc ttaagataca tgcaaaaaag catgtatctt                        280

<210> SEQ ID NO 14
<211> LENGTH: 210
<212> TYPE: DNA
<213> ORGANISM: Artificial Sequence
<220> FEATURE:
<223> OTHER INFORMATION: EBSnew x10 promoter

<400> SEQUENCE: 14
gtatcatgca atgaatcaac ctcttggttc aatgaatcga gtgcaatata cattgtatta    60
tgggatggat tcaatgcatc gttctctcaa ttcattgcac tcttatttaa atacaatgca   120
tcagtagtcc gattcattgc acaacgaatt ggatacaatg tatttgtgaa cagatacatt   180
gaacattagg agagatacat tgaatctata                                   210

<210> SEQ ID NO 15
<211> LENGTH: 210
<212> TYPE: DNA
<213> ORGANISM: Artificial Sequence
<220> FEATURE:
<223> OTHER INFORMATION: mutEBSnew x10 promoter

<400> SEQUENCE: 15
gtatcaggca atgactcaac ctcttggttg aacgaatcga gtgcaatata gattgtaata    60
tgggatggat taaacgcatc gttctctcaa ttcgtagcac tcttatttaa atactaggca    120
tcagtagtcc gattccttgc tcaacgaatt ggctacaatg taattgtgaa cagatagata    180
gaacattagg agagctacat tgaaactata    210

<210> SEQ ID NO 16
<211> LENGTH: 175
<212> TYPE: DNA
<213> ORGANISM: Artificial Sequence
<220> FEATURE:
<223> OTHER INFORMATION: EBSoriginal x5 promoter

<400> SEQUENCE: 16
cctcatgatc aaagggggga tgcactattt aagatcctca tgatcaaagg ggggatgcac    60
tatttaagat cctcatgatc aaagggggga tgcactattt aagatcctca tgatcaaagg    120
ggggatgcac tatttaagat cctcatgatc aaagggggga tgcactattt aagat    175

<210> SEQ ID NO 17
<211> LENGTH: 210
<212> TYPE: DNA
<213> ORGANISM: Artificial Sequence
<220> FEATURE:
<223> OTHER INFORMATION: 1 WT variant

<400> SEQUENCE: 17
gtatcatgca atgaatcatc ctcttggttc aatgaatcga gttcaatata cattgtatta    60
tgggattgat tcaatgcatt gttctctcaa ttcattgcac tcgtatttaa atacaatgca    120
tcattagtcc gattcattgc acaacaaatt ggatacaatg tatttgtcaa cagatacatt    180
gaacattagg agatatacat tgaatctata    210

<210> SEQ ID NO 18
<211> LENGTH: 210
<212> TYPE: DNA
<213> ORGANISM: Artificial Sequence
<220> FEATURE:
<223> OTHER INFORMATION: 2 WT variant

<400> SEQUENCE: 18
gtatcatgca atgaatcatc ctcttggttc aatgaatcga gttctcaatt cattgcactc    60
gtatttaaat acaatgcatc attagtccga ttcattgcac aacaaattgg atacaatgta    120
tttgtcaaca gatacattga acattaggat tgattcaatg cattgttctc aatatacatt    180
gtattatggg agatatacat tgaatctata    210

<210> SEQ ID NO 19
<211> LENGTH: 210
<212> TYPE: DNA
<213> ORGANISM: Artificial Sequence
<220> FEATURE:
<223> OTHER INFORMATION: 3 WT variant

<400> SEQUENCE: 19
tctcggtgca atgtattggt agtccgattc attgcacaac aaattggata caatgtattt    60
gtcaacagat acattgaaca ttaggattga ttcaatgcat tgttctcaat atacattgta    120
ttatgggtat catgcaatga atcatcctct tggttcaatg aatcgagttc tcaattcatt    180
gcactcgtag agatatacat tgaatctata    210

<210> SEQ ID NO 20

<211> LENGTH: 210
<212> TYPE: DNA
<213> ORGANISM: Artificial Sequence
<220> FEATURE:
<223> OTHER INFORMATION: 4 WT variant

<400> SEQUENCE: 20

```
tctcggtgca atgtattggt agtccgattc attgcacaac aaattggata caatgtattt      60
gtcaacagat acattgaaca ttaggattga ttcaatgcat tgttctcaat atacattgta     120
ttatgggtat catgcaatga atcatcctct tggttcaatg aatcgagttc tcaattcatt     180
gcactcgtag agatatacat tgaatctata                                      210
```

<210> SEQ ID NO 21
<211> LENGTH: 210
<212> TYPE: DNA
<213> ORGANISM: Artificial Sequence
<220> FEATURE:
<223> OTHER INFORMATION: 5 WT variant

<400> SEQUENCE: 21

```
tctcggtgca atgtattggt agtccgattc attgcacaac aaaacagata cattgaacat      60
taggattgat tcaatgcatt gttctcaata tacattgtat tatgggtatc atgcaatgaa     120
tcatcctctt ggttcaatga atcgagttct caattcattg cactcgtatt taaatacaat     180
gcatcattag agatatacat tgaatctata                                      210
```

<210> SEQ ID NO 22
<211> LENGTH: 210
<212> TYPE: DNA
<213> ORGANISM: Artificial Sequence
<220> FEATURE:
<223> OTHER INFORMATION: 6 WT variant

<400> SEQUENCE: 22

```
tcaatataca ttgtattatg ggtatcatgc aatgaatcat cctcttggtt caatgaatcg      60
agtgtccgat tcattgcaca acaaattgga tacaatgtat tgtcaacag atacattgaa     120
cattaggatt gattcaatgc attgttctct caattcattg cactcgtatt taaatacaat     180
gcatcattag agatatacat tgaatctata                                      210
```

<210> SEQ ID NO 23
<211> LENGTH: 210
<212> TYPE: DNA
<213> ORGANISM: Artificial Sequence
<220> FEATURE:
<223> OTHER INFORMATION: 7 WT variant

<400> SEQUENCE: 23

```
tctcggtgca atgtattggt agattgattc aatgcattgt tctcaatata cattgtatta      60
tgggtatcat gcaatgaatc atcctcttgg ttcaatgaat cgagttctca attcattgca     120
ctcgtagtcc gattcattgc acaacaaatt ggatacaatg tatttgtcaa cagatacatt     180
gaacattagg agatatacat tgaatctata                                      210
```

<210> SEQ ID NO 24
<211> LENGTH: 210
<212> TYPE: DNA
<213> ORGANISM: Artificial Sequence
<220> FEATURE:
<223> OTHER INFORMATION: 8 WT variant

<400> SEQUENCE: 24

| | |
|---|---|
| tcaatataca ttgtattatg ggtatcatgc aatgaatcat cctcttggtt caatgaatcg | 60 |
| agttctcaat tcattgcact cgtatttaaa tacaatgcat cattagattg attcaatgca | 120 |
| ttgttcgtcc gattcattgc acaacaaatt ggatacaatg tatttgtcaa cagatacatt | 180 |
| gaacattagg agatatacat tgaatctata | 210 |

<210> SEQ ID NO 25
<211> LENGTH: 210
<212> TYPE: DNA
<213> ORGANISM: Artificial Sequence
<220> FEATURE:
<223> OTHER INFORMATION: 9 WT variant

<400> SEQUENCE: 25

| | |
|---|---|
| tcaagattca atgaactccg ttctcaattc attgcactcg tatttaaata caatgcatca | 60 |
| ttagattgat tcaatgcatt gttctcaata tacattgtat tatgggtatc atgcaatgaa | 120 |
| tcatcctctt ggttcaatga atcgagtgtc cgattcattg cacaacaaaa cagatacatt | 180 |
| gaacattagg agatatacat tgaatctata | 210 |

<210> SEQ ID NO 26
<211> LENGTH: 210
<212> TYPE: DNA
<213> ORGANISM: Artificial Sequence
<220> FEATURE:
<223> OTHER INFORMATION: 10 WT variant

<400> SEQUENCE: 26

| | |
|---|---|
| tctcggtgca atgtattggt agtccgattc attgcacaac aaaacagata cattgaacat | 60 |
| taggattgat tcaatgcatt gttctctcaa ttcattgcac tcgtagaaag atacattgaa | 120 |
| tgcgaggtat catgcaatga atcatcctct tggttcaatg aatcgagttc aatatacatt | 180 |
| gtattatggg agatatacat tgaatctata | 210 |

<210> SEQ ID NO 27
<211> LENGTH: 210
<212> TYPE: DNA
<213> ORGANISM: Artificial Sequence
<220> FEATURE:
<223> OTHER INFORMATION: EBSnew variant 1a

<400> SEQUENCE: 27

| | |
|---|---|
| gtatcatgca atgaatcatc ctcctggttc aatgaatcga gttcaaaata cattgtatta | 60 |
| tggggttgat tcaatgcatt gttcgctcaa ttcattgcac tcttatttaa atacaatgca | 120 |
| tccttagtcc gattcattgc acaacgaatt ggatacaatg tatttgtaaa cagatacatt | 180 |
| gaacattatg agatatacat tgaatctata | 210 |

<210> SEQ ID NO 28
<211> LENGTH: 210
<212> TYPE: DNA
<213> ORGANISM: Artificial Sequence
<220> FEATURE:
<223> OTHER INFORMATION: EBSnew variant 2a

<400> SEQUENCE: 28

| | |
|---|---|
| gtatcatgca atgaatcatc ctcctggttc aatgaatcga gctctcaatt cattgcactc | 60 |
| ttatttaaat acaatgcatc cttagtccga ttcattgcac aacgaattgg atacaatgta | 120 |
| tttgtaaaca gatacattga acagtaggat tgattcaatg cattgtgctc aatatacatt | 180 |

```
<210> SEQ ID NO 29
<211> LENGTH: 210
<212> TYPE: DNA
<213> ORGANISM: Artificial Sequence
<220> FEATURE:
<223> OTHER INFORMATION: EBSnew variant 3a

<400> SEQUENCE: 29
tctcggtgca atgtattggt agcccgattc attgcacaac gaattggata caatgtattt    60
gtaaacagat acattgaaca tttggattga ttcaatgcat tgttctctat atacattgta   120
ttatgggtat tatgcaatga atcaacctct tggttcaatg aatcgagtgc tcaattcatt   180
gcactcatag agatatacat tgaatctata                                    210

<210> SEQ ID NO 30
<211> LENGTH: 210
<212> TYPE: DNA
<213> ORGANISM: Artificial Sequence
<220> FEATURE:
<223> OTHER INFORMATION: EBSnew variant 4a

<400> SEQUENCE: 30
tctcggtgca atgtattggt agcccgattc attgcacaac gaattggata caatgtattt    60
gtaaacagat acattgaaca ttagtattga ttcaatgcat tgttctctat atacattgta   120
ttatgggtat tatgcaatga atcatcttct tggttcaatg aatcgagtgc tcaattcatt   180
gcactcatag agatatacat tgaatctata                                    210

<210> SEQ ID NO 31
<211> LENGTH: 210
<212> TYPE: DNA
<213> ORGANISM: Artificial Sequence
<220> FEATURE:
<223> OTHER INFORMATION: EBSnew variant 5a

<400> SEQUENCE: 31
tctcggtgca atgtattggt agcccgattc attgcacaat aaaacagata cattgaacaa    60
taggattgat tcaatgcatt gttctctata tacattgtat tatgggtatt atgcaatgaa   120
tcatcctcct ggttcaatga atcgagtgct caattcattg cactcttatt taaatacaat   180
gcatcagtag agatatacat tgaatctata                                    210

<210> SEQ ID NO 32
<211> LENGTH: 210
<212> TYPE: DNA
<213> ORGANISM: Artificial Sequence
<220> FEATURE:
<223> OTHER INFORMATION: EBSnew variant 6a

<400> SEQUENCE: 32
tcaatataca ttgtattatg ggtataatgc aatgaatcat cttcttggtt caatgaatcg    60
ggtgtccgat tcattgcaca acgaattgga tacaatgtat tgtgaacag atacattgaa   120 cattagtatt gattcaatgc attgttctct ctattcattg cactcgtttt taaatacaat   180
gcatcagtag agatatacat tgaatctata                                    210

<210> SEQ ID NO 33
<211> LENGTH: 210
<212> TYPE: DNA
<213> ORGANISM: Artificial Sequence
```

```
<220> FEATURE:
<223> OTHER INFORMATION: EBSnew variant 7a

<400> SEQUENCE: 33
tctcggtgca atgtattcgt agattgattc aatgcattgt tctctatata cattgtatta      60
tgggtattat gcaatgaatc atcctcctgg ttcaatgaat cgagttctct attcattgca     120
ctcgtagtcc aattcattgc acaacgaatt ggatacaatg tatttgtaaa cagatacatt     180
gaacattagg agagatacat tgaatctata                                      210

<210> SEQ ID NO 34
<211> LENGTH: 210
<212> TYPE: DNA
<213> ORGANISM: Artificial Sequence
<220> FEATURE:
<223> OTHER INFORMATION: EBSnew variant 8a

<400> SEQUENCE: 34
tcaatataca ttgtattatg ggtataatgc aatgaatcac cctcttggtt caatgaatcg      60
agttctccat tcattgcact cctatttaaa tacaatgcat ccttagattg attcaatgca     120
ttgttcttcc gattcattgc acaacgaatt ggatacaatg tatttgtgaa cagatacatt     180
gaacattagg agagatacat tgaatctata                                      210

<210> SEQ ID NO 35
<211> LENGTH: 210
<212> TYPE: DNA
<213> ORGANISM: Artificial Sequence
<220> FEATURE:
<223> OTHER INFORMATION: EBSnew variant 9a

<400> SEQUENCE: 35
tcaagattca atgaactcct ttctcaattc attgcactag tatttaaata caatgcatca      60
gtagattgat tcaatgcatt gttctctata tacattgtat tatgggtatt atgcaatgaa     120
tcaacctctt ggttcaatga atcgagtgtc caattcattg cacaataaaa cagatacatt     180
gaacattatg agatatacat tgaatctata                                      210

<210> SEQ ID NO 36
<211> LENGTH: 210
<212> TYPE: DNA
<213> ORGANISM: Artificial Sequence
<220> FEATURE:
<223> OTHER INFORMATION: EBSnew variant 10a

<400> SEQUENCE: 36
tctcggtgca atgtattggt agcccgattc attgcacaat aaaacagata cattgaacat      60
ttggattgat tcaatgcatt gttctctgaa ttcattgcac tcgtagcaag atacattgaa     120
tgcgaggtat aatgcaatga atcatcctct tgttcaatg aatcgagctc aatatacatt      180
gtattatggg agaaatacat tgaatctata                                      210

<210> SEQ ID NO 37
<211> LENGTH: 210
<212> TYPE: DNA
<213> ORGANISM: Artificial Sequence
<220> FEATURE:
<223> OTHER INFORMATION: EBSnew variant 1b

<400> SEQUENCE: 37
gtatcatgca atgaatcaac ctcttggttc aatgaatcga gttcattata cattgtatta      60
```

```
tgggatggat tcaatgcata gttctctcaa ttcattgcac tcttatttaa atacaatgca    120
tccttagtcc gattcattgc acaacgaatt ggatacaatg tatttgtgaa cagatacatt    180
gaacaatagg agatatacat tgaatctata                                     210
```

```
<210> SEQ ID NO 38
<211> LENGTH: 210
<212> TYPE: DNA
<213> ORGANISM: Artificial Sequence
<220> FEATURE:
<223> OTHER INFORMATION: EBSnew variant 2b

<400> SEQUENCE: 38
gtatcatgca atgaatcaac ctcttggttc aatgaatcga gtgctcaatt cattgcactc    60
ttatttaaat acaatgcatc cttagtccga ttcattgcac aacgaattgg atacaatgta    120
tttgtaaaca gatacattga acattagtat tgattcaatg cattgtgctc aatatacatt    180
gtattatgag agatatacat tgaatctata                                     210
```

```
<210> SEQ ID NO 39
<211> LENGTH: 210
<212> TYPE: DNA
<213> ORGANISM: Artificial Sequence
<220> FEATURE:
<223> OTHER INFORMATION: EBSnew variant 3b

<400> SEQUENCE: 39
tcaagattca atgaactcct ttctcaattc attgcactct tagattgatt caatgcattg    60
ttctctatat acattgtatt atgggtatta tgcaatgaat catcctcctg gttcaatgaa    120
tcgagtgtcc aattcattgc acaacgaatt ggatacaatg tatttgtaaa cagatacatt    180
gaacataagg agatatacat tgaatctata                                     210
```

```
<210> SEQ ID NO 40
<211> LENGTH: 210
<212> TYPE: DNA
<213> ORGANISM: Artificial Sequence
<220> FEATURE:
<223> OTHER INFORMATION: EBSnew variant 4b

<400> SEQUENCE: 40
tctcggtgca atgtattggt agtgcgattc attgcacaac gaattggata caatgtattt    60
gtaaacagat acattgaaca gtaggattga ttcaatgcat tgttctctat atacattgta    120
ttatgggtat tatgcaatga atcatcctcc tggttcaatg aatcgagtgc tcaattcatt    180
gcactcatag agatatacat tgaatctata                                     210
```

```
<210> SEQ ID NO 41
<211> LENGTH: 210
<212> TYPE: DNA
<213> ORGANISM: Artificial Sequence
<220> FEATURE:
<223> OTHER INFORMATION: EBSnew variant 5b

<400> SEQUENCE: 41
tctcggtgca atgtattgga agtccgattc attgcacaat aaaacagata cattgaacat    60
taggactgat tcaatgcatt gttctctata tacattgtat tatgggtatt atgcaatgaa    120
tcaacctctt ggttcaatga atcgagtgct caattcattg cactcttatt taaatacaat    180
gcatcaatag agatatacat tgaatctata                                     210
```

<210> SEQ ID NO 42
<211> LENGTH: 210
<212> TYPE: DNA
<213> ORGANISM: Artificial Sequence
<220> FEATURE:
<223> OTHER INFORMATION: EBSnew variant 6b

<400> SEQUENCE: 42

```
tcaatataca ttgtattatg ggtataatgc aatgaatcat cctattggtt caatgaatcg      60
agtgttcgat tcattgcaca acgaattgga tacaatgtat ttgtgaacag atacattgaa     120
cattagaatt gattcaatgc attgttctca caattcattg cactcctatt taaatacaat     180
gcatcactag agatatacat tgaatctata                                      210
```

<210> SEQ ID NO 43
<211> LENGTH: 210
<212> TYPE: DNA
<213> ORGANISM: Artificial Sequence
<220> FEATURE:
<223> OTHER INFORMATION: EBSnew variant 7b

<400> SEQUENCE: 43

```
tctcggtgca atgtattggt agcttgattc aatgcattgt tctctatata cattgtatta      60
tgggtattat gcaatgaatc accctcttgg ttcaatgaat cgagttctta attcattgca     120
ctagtagtcc gattcattgc acaacgaatt ggatacaatg tatttgtgaa cagatacatt     180
gaacattatg agatatacat tgaatctata                                      210
```

<210> SEQ ID NO 44
<211> LENGTH: 210
<212> TYPE: DNA
<213> ORGANISM: Artificial Sequence
<220> FEATURE:
<223> OTHER INFORMATION: EBSnew variant 8b

<400> SEQUENCE: 44

```
tcaatataca ttgtattatg ggtataatgc aatgaatcat gctcttggtt caatgaatcg      60
agttcttaat tcattgcact cgttttttaaa tacaatgcat cactagattg attcaatgca     120
tagttcgtcc gattcattgc acaacgaatt ggatacaatg tatttgtaaa cagatacatt     180
gaacagtagg agatatacat tgaatctata                                      210
```

<210> SEQ ID NO 45
<211> LENGTH: 210
<212> TYPE: DNA
<213> ORGANISM: Artificial Sequence
<220> FEATURE:
<223> OTHER INFORMATION: EBSnew variant 9b

<400> SEQUENCE: 45

```
tcaagattca atgaactcct ttctcaattc attgcactcg tttttaaata caatgcatca      60
gtagattgat tcaatgcatt gttctctata tacattgtat tatgggtatt atgcaatgaa     120
tcctcctctt ggttcaatga atcgagtgtt cgattcattg cacaataaaa cagatacatt     180
gaacattagg agagatacat tgaatctata                                      210
```

<210> SEQ ID NO 46
<211> LENGTH: 210
<212> TYPE: DNA
<213> ORGANISM: Artificial Sequence
<220> FEATURE:
<223> OTHER INFORMATION: EBSnew variant 10b

```
<400> SEQUENCE: 46
tctcggtgca atgtattgga agtccgattc attgcacaat aaaacagata cattgaacat    60
caggattgat tcaatgcatt gttctctcta ttcattgcac tcgtagtaag atacattgaa   120
tgcgaggtat aatgcaatga atcatcctat tggttcaatg aatcgagtgc aatatacatt   180
gtattatggg cgatatacat tgaatctata                                    210

<210> SEQ ID NO 47
<211> LENGTH: 11
<212> TYPE: DNA
<213> ORGANISM: Artificial Sequence
<220> FEATURE:
<223> OTHER INFORMATION: BsmBI restriction site
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 47
nnnncgtctc n                                                         11

<210> SEQ ID NO 48
<211> LENGTH: 111
<212> TYPE: DNA
<213> ORGANISM: Artificial Sequence
<220> FEATURE:
<223> OTHER INFORMATION: Formula I
<220> FEATURE:
<221> NAME/KEY: misc_feature
<222> LOCATION: (1)..(50)
<223> OTHER INFORMATION: n is a, c, g, or t; each nucleotide in
      positions 1-50 is either absent or present
<220> FEATURE:
<221> NAME/KEY: misc_feature
<222> LOCATION: (62)..(111)
<223> OTHER INFORMATION: n is a, c, g, or t; each nucleotide in
      positions 62-111 is either absent or present

<400> SEQUENCE: 48
nnnnnnnnnn nnnnnnnnnn nnnnnnnnnn nnnnnnnnnn nnnnnnnnnn rtdcawtgha    60
ynnnnnnnnn nnnnnnnnnn nnnnnnnnnn nnnnnnnnnn nnnnnnnnnn n            111

<210> SEQ ID NO 49
<211> LENGTH: 12
<212> TYPE: DNA
<213> ORGANISM: Artificial Sequence
<220> FEATURE:
<223> OTHER INFORMATION: 2EBS[-1]

<400> SEQUENCE: 49
rtwcawtgwa yc                                                        12

<210> SEQ ID NO 50
<211> LENGTH: 12
<212> TYPE: DNA
<213> ORGANISM: Artificial Sequence
<220> FEATURE:
<223> OTHER INFORMATION: TEIL-LIKE

<400> SEQUENCE: 50
atgaatctkg ac                                                        12
```

```
<210> SEQ ID NO 51
<211> LENGTH: 12
<212> TYPE: DNA
<213> ORGANISM: Artificial Sequence
<220> FEATURE:
<223> OTHER INFORMATION: GC-EBS
<220> FEATURE:
<221> NAME/KEY: misc_feature
<222> LOCATION: (11)..(11)
<223> OTHER INFORMATION: n is a, c, g, or t

<400> SEQUENCE: 51
rrkrratgaa ny                                                        12
```